(12) United States Patent
Krishnan et al.

(10) Patent No.: US 8,153,437 B2
(45) Date of Patent: Apr. 10, 2012

(54) DNA-BASED MOLECULAR SWITCHES AND USES THEREOF

(75) Inventors: Yamuna Krishnan, Bangalore (IN); Saikat Chakraborty, Bangalore (IN)

(73) Assignee: National Center for Biological Sciences, Bangalore (IN)

( * ) Notice: Subject to any disclaimer, the term of this patent is extended or adjusted under 35 U.S.C. 154(b) by 4 days.

(21) Appl. No.: 12/720,952

(22) Filed: Mar. 10, 2010

(65) Prior Publication Data

US 2011/0223676 A1 Sep. 15, 2011

(51) Int. Cl.
*G01N 33/00* (2006.01)

(52) U.S. Cl. .............................. 436/94; 422/12; 436/163

(58) Field of Classification Search ........................ None
See application file for complete search history.

(56) References Cited

U.S. PATENT DOCUMENTS

| | | | |
|---|---|---|---|
| 5,625,051 | A | 4/1997 | Gehring et al. |
| 7,122,461 | B2 | 10/2006 | Dubin |
| 7,223,544 | B2 | 5/2007 | Luo et al. |
| 7,272,511 | B2 | 9/2007 | Occhipinti et al. |
| 2006/0029933 | A1 | 2/2006 | Borer et al. |
| 2006/0216692 | A1 | 9/2006 | Borer et al. |

OTHER PUBLICATIONS

Gfrorer et al. "Structural transitions and ph-dependent equilibria between unusual double and triple helical conformations of nucleic acid polymers, studied by UV resonance raman spectroscopy". 1993. Applied Spectroscopy. vol. 47. pp. 1064-1070.*

Al, Hui-wang et al., "Fluorescent protein FRET pairs for ratiometric imaging of dual biosensors," *Nature Methods*, vol. 5, No. 5, May 2008, pp. 401-403.
Alberti, Patrizia et al., "DNA duplex-quadruplex exchange as the basis for a nanomolecular machine," *PNAS*, vol. 100, No. 4, Feb. 18, 2003, pp. 1569-1573.
Alderfer, James L. et al., "A Proton Magnetic Resonance Study of Polydeoxyriboadenylic Acid," *Journal of the American Chemical Society*, vol. 93, No. 26, Dec. 29, 1971, pp. 7305-7314.
Allan, Victoria J. et al., "Membrane motors," *Current Opinion in Cell Biology*, vol. 11, 1999, pp. 476-482.
Altan, Nihal et al., "Defective Acidification in Human Breast Tumor Cells and Implications for Chemotherapy," *J. Exp. Med.*, vol. 187, No. 10, May 18, 1998, pp. 1583-1598.
Bath, Jonathan et al., "DNA nanomachines," *Nature Nanotechnology*, vol. 2, May 2007, pp. 275-284.
Benenson, Yaakov et al., "An autonomous molecular computer for logical control of gene expression," *Nature*, vol. 429, May 27, 2004, pp. 423-429.
Beyer, Stefan et al., "A modular DNA signal translator for the controlled release of a protein by an aptamer," *Nucleic Acids Research*, vol. 34, No. 5, 2006, pp. 1581-1587.
Bhatia, Dhiraj et al., "Icosahedral DNA Nanocapsules by Modular Assembly," *Angew. Chem. Int. Ed.*, vol. 48, 2009, pp. 1-5.

(Continued)

*Primary Examiner* — Yelena G Gakh
*Assistant Examiner* — David Weisz
(74) *Attorney, Agent, or Firm* — Foley & Lardner LLP

(57) ABSTRACT

Disclosed are nucleic acid-based molecular switches that respond to changes in pH. The switches may be used in DNA nanodevices. The switches may also act as sensors for measuring the pH of a sample, including cells, regions thereof, and whole organisms. The switch includes an A-motif that forms at acidic pH. Also disclosed are compositions and methods for measuring the pH of cells or regions thereof, such as vesicles, the nucleus, mitochondrial matrix, or the Golgi lumen.

19 Claims, 20 Drawing Sheets

OTHER PUBLICATIONS

Brasuel, Murphy et al., "Fluorescent Nanosensors for Intracellular Chemical Analysis: Decyl Methacrylate Liquid Polymer Matrix and Ion-Exchange-Based Potassium PEBBLE Sensors with Real-Time Application to Viable Rat C6 Glioma Cells," *Analytical Chemistry*, vol. 73, No. 10, May 15, 2001, pp. 2221-2228.

Bush, C. Allen et al., "Optical Activity of Single-Stranded Polydeoxyadenylic and Polyriboadenylic Acids; Dependence of Adenine Chromophore Cotton Effects on Polymer Conformation," *Biopolymers*, vol. 7, 1969, pp. 395-409.

Chakraborty, Saikat et al., Kinetic hybrid i-motifs: Intercepting DNA with RNA to form a $DNA_2$-$RNA_2$ i-motif, *Biochimie*, vol. 90, 2008, pp. 1088-1095.

Chakraborty, Saikat et al., "The poly dA helix: a new structural motif for high performance DNA-based molecular switches," *Nucleic Acids Research*, Mar. 11, 2009, pp. 1-8.

Chen, Yi et al., "A DNA Nanomachine Based on a Duplex-Triplex Transition," *Angew. Chem. Int. Ed.*, vol. 43, 2004, pp. 5335-5338.

Clark, Heather A. et al., "Optical Nanosensors for Chemical Analysis inside Single Living Cells. 2. Sensors for pH and Calcium and the Intracellular Application of PEBBLE Sensors," *Analytical Chemistry*, vol. 71, No. 21, Nov. 1, 1999, pp. 4837-4843.

Disbrow, Gary L. et al., "Endoplasmic Reticulum-Localized Human Papillomavirus Type 16 E5 Protein Alters Endosomal pH but Not *trans*-Golgi pH," *Journal of Virology*, vol. 79, No. 9, May 2005, pp. 5839-5846.

Downey, Gregory P. et al., "Phagosomal Maturation, Acidification, and Inhibition of Bacterial Growth in Nanphagocytic Cells Transfected with FcγRIIA Receptors," *The Journal of Biological Chemistry*, vol. 274, No. 40, Oct. 1, 1999, pp. 28436-28444.

Fresco, Jacques R., "Polynucleotides II: The X-Ray Diffraction Patterns of Solutions of the Randomly Coiled and Helical Forms of Polyriboadenylic Acid," *J. Mol. Biol.*, vol. 1, 1959, pp. 106-110.

Gehring, Kalle et al., "A tetrameric DNA structure with protonated cytosine-cytosine base pairs," *Nature*, vol. 363, Jun. 10, 1993, pp. 561-565.

Ghodke, Harshad B. et al., "The I-Tetraplex Building Block: Rational Design and Controlled Fabrication of Robust 1D DNA Scaffolds through Non-Watson—Crick Interactions," *Angew. Chem. Int. Ed.*, vol. 46, 2007, pp. 2646-2649.

Grant, Roberta L. et al., "Ratiometric Measurement of Intracellular pH of Cultured Cells with BCECF in a Fluorescence Multi-Well Plate Reader," *In Vitro Cell Dev. Biol.*, vol. 33, Apr. 1997, pp. 256-260.

Griesbeck, Oliver, "Fluorescent proteins as sensors for cellular functions," *Current Opinion in Neurobiology*, vol. 14, 2004, pp. 636-641.

Kneen, Melea et al., "Green Fluorescent Protein as a Noninvasive Intracellular pH Indicator," *Biophysical Journal*, vol. 74, Mar. 1998, pp. 1591-1599.

Koo, Mei K. et al., "Simultaneous Analysis of Steady-State Intracellular pH and Cell Morphology by Automated Laser Scanning Cytometry," *International Society for Analytical Cytology*, 2007, pp. 87-93.

Liedl, Tim et al., "Switching the Conformation of a DNA Molecule with a Chemical Oscillator," *Nano Lett.*, vol. 5, No. 10, 2005, pp. 1894-1898.

Lin, Jie, "Recent development and applications of optical and fiber-optic pH sensors," *Trends in Analytical Chemistry*, vol. 19, No. 9, 2000, pp. 541-552.

Liu, Juewen et al., "A Colorimetric Lead Biosensor Using DNAzyme-Directed Assemble of Gold Nanoparticles," *J. Am. Chem. Soc.*, vol. 125, No. 22, 2003, pp. 6642-6643.

Liu, Dongsheng et al., "A Proton-Fuelled DNA Nanomachine," *Angew. Chem. Int. Ed.*, vol. 42, 2003, pp. 5734-5736.

Luo, Jia et al., "NMR study of self-paired parallel duplex of d(AAAAACCCCC) in solution," *FEBS Letters*, vol. 306, No. 2,3, Jul. 1992, pp. 223-228.

Mao, Chengde et al., "A nonmechanical device based on the B-Z transition of DNA", *Nature*, vol. 397, Jan. 14, 1999, pp. 144-146.

Matsuyama, S. et al., "Mitochondria-dependent apoptosis and cellular pH regulation," *Cell Death and Differentiation*, vol. 7, 2000, pp. 1155-1165.

Miesenböck, Gero et al., "Visualizing secretion and synaptic transmission with pH-sensitive green fluorescent proteins," *Nature*, vol. 394, Jul. 9, 1998, pp. 192-195.

Modi, Souvik et al., "The PNA-DNA hybrid I-motif: implications for sugar-sugar contacts in i-motif tetramerization," *Nucleic Acids Research*, vol. 34, No. 16, 2006, pp. 4354-4363.

Modi, Souvik et al., "A DNA nanomachine that maps spatial and temporal pH changes inside living cells," *Nature Nanotechnology*, Apr. 6, 2009, pp. 1-6.

Murphy, Robert F. et al., "Endosome pH Measured in Single Cells by Dual Fluorescence Flow Cytometry: Rapid Acidification of Insulin to pH 6," *The Journal of Cell Biology*, vol. 98, May 1984, pp. 1757-1762.

Ohkuma, Shoji et al., "Fluorescence probe measurement of the intralysosomal pH in living cells and the perturbation of pH by various agents", *Proc. Natl. Acad. Sci. USA*, vol. 75, No. 7, Jul. 1978, pp. 3327-3331.

Olsthoorn, Cornelis S. et al., "Conformational Characteristics of the Trinucleoside Diphosphate dApdApdA and Its Constituents from Nuclear Magnetic Resonance and Circular Dichroism Studies," *Eur. J. Biochem.*, vol. 112, 1980, pp. 95-110.

Overly, Caroline C. et al., "Quantitative measurement of intraorganelle pH in the endosomal-lysosomal pathway in neurons by using ratiometric imaging with pyranine," *Proc. Natl. Acad. Sci. USA*, vol. 92, Apr. 1995, pp. 3156-3160.

Paul, Alexis et al., "Combining G-Quadruplex Targeting Motifs on a Single Peptide Nucleic Acid Scaffold: A Hybrid (3+1) PNA-DNA Bimolecular Quadruplex," *Chem. Eur. J.*, vol. 14, 2008, pp. 8682-8689.

Pitchiaya, Sethuramasundaram et al., "First blueprint, now bricks: DNA as construction material on the nanoscale," *Chem. Soc. Rev.*, vol. 35, 2006, pp. 1111-1121.

Rich, Alexander et al., "The Molecular Structure of Polyadenylic Acid," *J. Mol. Biol.*, vol. 3, 1961, pp. 71-86.

Robinson, Howard et al., "5'-CGA sequence is a strong motif for homo base-paired parallel-stranded DNA duplex as revealed by NMR analysis," *Proc. Natl. Acad. Sci. USA*, vol. 90, Jun. 1993, pp. 5224-5228.

Roos, Albert et al., "Intracellular pH," *Physiological Reviews*, vol. 61, No. 2, Apr. 1981, pp. 296-434.

Sachs, Alan et al., "Poly(A) Tail Metabolism and Function in Eucaryotes," *The Journal of Biological Chemistry*, vol. 268, No. 31, Nov. 5, 1993, pp. 22955-22958.

Saenger, W. et al., "A Structural Model for the Polyadenylic Acid Single Helix," *J. Mol. Biol.*, vol. 93, 1975, pp. 529-534.

Shih, William, "Dynamic DNA," *Nature Materials*, vol. 7, Feb. 2008, pp. 98-100.

Sipe, David M. et al., "High-resolution kinetics of transferrin acidification in BALB/c 3T3 cells: Exposure to pH 6 followed by temperature-sensitive alkalinization during recycling," *Proc. Natl. Acad. Sci. USA*, vol. 84, Oct. 1987, pp. 7119-7123.

Snoussi, K. et al., "The RNA i-motif," *J. Mol. Biol.*, vol. 309, 2001, pp. 139-153.

Srivastava, Jyoti et al., "Intracellular pH Sensors: Design Principles and Functional Significance," *Physiology*, vol. 22, Feb. 2007, pp. 30-39.

Tan, Weihong et al., "Submicrometer Intracellular Chemical Optical Fiber Sensors," *Science*, vol. 258, Oct. 30, 1992, pp. 778-781.

Thomas, John A. et al., "Intracellular pH Measurements in Ehrlich Ascites Tumor Cells Utilizing Spectroscopic Probes Generated in Situ," *Biochemistry*, vol. 18, No. 11, 1979, pp. 2210-2218.

Walker, David J. et al., "Simultaneous Measurement of Intracellular pH and $K^+$ or $NO_3$ in Barley Root Cells Using Triple-Barreled, Ion-Selective Microelectrodes," *Plant Physiol.*, vol. 108, 1995, pp. 743-751.

Xue, Lin et al., "A ratiometric fluorescent sensor with a large Stokes shift for imaging zinc ions in living cells," *Chem. Commun.*, 2009, pp. 1061-1063.

Yin, Peng et al., "Programming biomolecular self-assembly pathways," *Nature*, vol. 451, Jan. 17, 2008, pp. 318-323.

Yurke, Bernard et al., "A DNA-fuelled molecular machine made of DNA," *Nature*, vol. 406, Aug. 10, 2000, pp. 605-608.

Zimmerman, Steven B. et al., "An Ordered Single-stranded Structure for Polyadenylic Acid in Denaturing Solvents. An X-ray Fiber Diffraction and Model Building Study," *J. Mol. Biol.*, vol. 116, 1977, pp. 317-330.

Callahan et al., "B- to Z-DNA transition probed by oligonucleotides containing methylphosphonates", Biochemistry, *Proc. Natl. Acad. Sci. USA*, (Mar. 1986), vol. 83, pp. 1617-1621.

Mao et al., "A nanomechanical device based on the B-Z transition of DNA", letters to nature, *Nature*, (Jan. 14, 1999), vol. 397, pp. 144-146.

* cited by examiner 15 mer

DNA-BASED MOLECULAR SWITCHES AND USES THEREOF

TECHNICAL FIELD

This disclosure relates generally to methods, kits and compositions pertaining to molecular switches. The disclosure also relates to nanoscale DNA architectures that comprise molecular switches.

BACKGROUND

The following description is provided to assist the understanding of the reader. None of the information provided or references cited is admitted to be prior art.

One aim of biotechnology and nanotechnology is a rational approach to the construction of new biomaterials, including individual objects and nanomechanical devices. Intricate arrangements of atoms could serve many practical purposes. The informational macromolecules of biological systems, proteins and nucleic acids, are believed to have the potential to serve as building blocks for these constructions, because they are used for similar purposes in the cell. Structural DNA nanotechnology is an emerging field that uses DNA to create either rigid architectures or dynamic switches. Dynamic, DNA-based nanodevices may also be described as molecular switches. They are based on structural transitions between two well-defined conformations of DNA upon the application of a stimulus. For instance, nanometer-scale circuitry and robotics could accomplish many tasks that are impossible today. One can envision improvements in the storage and retrieval of information, understanding of the molecular basis of medical problems, and the assembly of very smart materials as possible end products of the ability to control the structure of matter on the nanometer scale.

SUMMARY

The compositions and methods described herein are based on the discovery that a parallel-stranded double helix of poly dA nucleic acid or "A-motif" shows reversible changes in conformation in response to pH. DNA strands can be hybridized on cue with a pH change and melted on cue with another pH change. Thus, the A-motif may be used in nanoscale DNA architectures that can self-assemble and dis-assemble on externally added pH cues.

In one aspect, the present disclosure provides a molecular switch comprising at least two poly dA nucleic acids, wherein the at least two poly dA nucleic acids are adapted to vary between first and second conformations in response to a change in pH. For example, the first and second conformations may be a parallel-stranded double helix and a single helix, respectively. In one embodiment, the at least two poly dA nucleic acids are in a parallel-stranded double helix conformation at acidic pH and the at least two poly dA nucleic acids are in single helix conformation at neutral pH.

In some embodiments, the at least two poly dA nucleic acids each comprise at least 10 consecutive dA nucleobases. In one embodiment, the at least two poly dA nucleic acids each comprise from about 10 to about 20 consecutive dA nucleobases. In an illustrative embodiment, the at least two poly dA nucleic acids each comprise 15 consecutive dA nucleobases.

In some embodiments, the molecular switch further comprises a signaling system. In one embodiment, the signaling system comprises an interacting label pair. In one embodiment, the interacting label pair is capable of energy transfer. In one embodiment, the interacting label pair is a fluorophore and quencher pair. In an illustrative embodiment, the fluorophore and the quencher are on separate poly dA nucleic acids, such that a difference in a fluorescent signal is detectable upon a change in conformation of the molecular switch. For example, the fluorophore may be selected from the group consisting of: FAM, HEX, TMR, TAMRA, ROX, Cy3, Cy5, and Texas Red. For example, the quencher may be selected from the group consisting of: DABCYL, QSY-7 and a Black-Hole dye. In some embodiments, the fluorophore and the quencher are conjugated to the at least two poly dA nucleic acids via a $C_3$ linker.

In one embodiment, the molecular switch further comprises a tagging moiety for linking the molecular switch to other biomolecules. In one embodiment, the tagging moiety is biotin and the molecular switch is linked to other biomolecules by binding to avidin or streptavidin.

In another aspect, the present disclosure provides a nucleic acid assembly comprising one or more modules that include an A-motif forming nucleic acid, wherein the A-motif forming nucleic acid is adapted to vary between first and second stable conformations in response to a change in pH. In one embodiment, two or more modules are joined to form a 1D, 2D or 3D architecture. In one embodiment, the module is a three-way junction with A-motif forming cohesive ends. In one embodiment, the module comprises a nucleic acid polymer capable of undergoing Watson-Crick base pairing. In one embodiment, at least one module is linked to a substrate. In some embodiments, the modules may include a molecular structure selected from the group consisting of a single stranded nucleic acid, a double-stranded nucleic acid, and a polypeptide.

In one aspect, the present disclosure provides a method for determining the pH of a sample, the method comprising: contacting the sample with one or more indicators having at least two poly dA nucleic acid strands conjugated to a signaling system, wherein the one or more indicators are adapted to vary between first and second stable conformations in response to a change in pH; and detecting the presence, absence, or magnitude of a signal from the signaling system to determine the pH of the sample. In one embodiment, the detecting comprises measuring the magnitude of the signal generated, wherein the magnitude indicates the pH of the sample. In one embodiment, the magnitude of the signal changes as the pH varies from pH 2 to 10. In one embodiment, the magnitude of the signal changes as the pH varies from pH 5 to 7. The sample may be in vitro or in vivo.

In another aspect, the present disclosure provides a method for determining the pH of a cell or region thereof comprising: contacting the cell or region thereof with one or more indicators having at least two poly dA nucleic acid strands conjugated to a signaling system, wherein the one or more indicators are adapted to vary between first and second stable conformations in response to a change in pH; and detecting the presence, absence, or magnitude of a signal from the signaling system to determine the pH of the cell or region thereof. In some embodiments, the one or more indicators further comprise one or more of a fusogenic peptide, a membrane-permeabilizing peptide, a sub-cellular localization sequence, or a cell-receptor ligand. In one embodiment, the sub-cellular localization sequence targets the indicator to a region of the cell selected from the group consisting of: the cytosol, the endoplasmic reticulum, the mitochondrial matrix, the chloroplast lumen, the medial trans-Golgi cisternae, the lumen of lysosome, and the lumen of an endosome. In one embodiment, the sub-cellular localization sequence is selected from the group consisting of a receptor ligand, a nuclear localization sequence (NLS), a nuclear export signal (NES), a plasma membrane targeting signal, a histone binding protein, and a nuclear protein. In one embodiment, the fusogenic peptide is a peptide of a viral protein derived from a virus selected from the group consisting of an influenza virus, a vesicular stomatitis virus, and an alphavirus. In one embodiment, the fusogenic peptide is a hemagglutinin of an influenza virus or a glycoprotein of a vesicular stomatitis virus. In one embodiment, the cell is a eukaryotic cell. In one embodiment, the eukaryotic cell is a mammalian cell.

In one aspect, the present disclosure provides a kit for measuring the pH of a sample, the kit comprising at least two poly dA nucleic acid strands conjugated to a signaling system, wherein the one or more indicators are adapted to vary between first and second stable conformations in response to a change in pH.

In one aspect, the disclosure proves a cell or an organism transfected with one or more indicators having at least two poly dA nucleic acid strands conjugated to a signaling system, wherein the one or more indicators are adapted to vary between first and second stable conformations in response to a change in pH.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE FIGURES

FIG. 14A shows adenines base-pairing via their reverse Watson-Crick faces where N1 (indicated by black arrow) is involved in H-bonding with N6H. FIG. 14B shows adenines base-pairing via their reverse Hoogsteen faces where N1 (indicated by black arrow) is not involved in H-bonding and hence available for protonation; and N6H (indicated by red arrow) can interact with ⁻O—P as seen in poly r(AH⁺—H⁺A). FIG. 14C shows a partial 1D spectrum (800 MHz Bruker) showing two different adenine $NH_{2b}$ protons.

DETAILED DESCRIPTION

Figure 1:
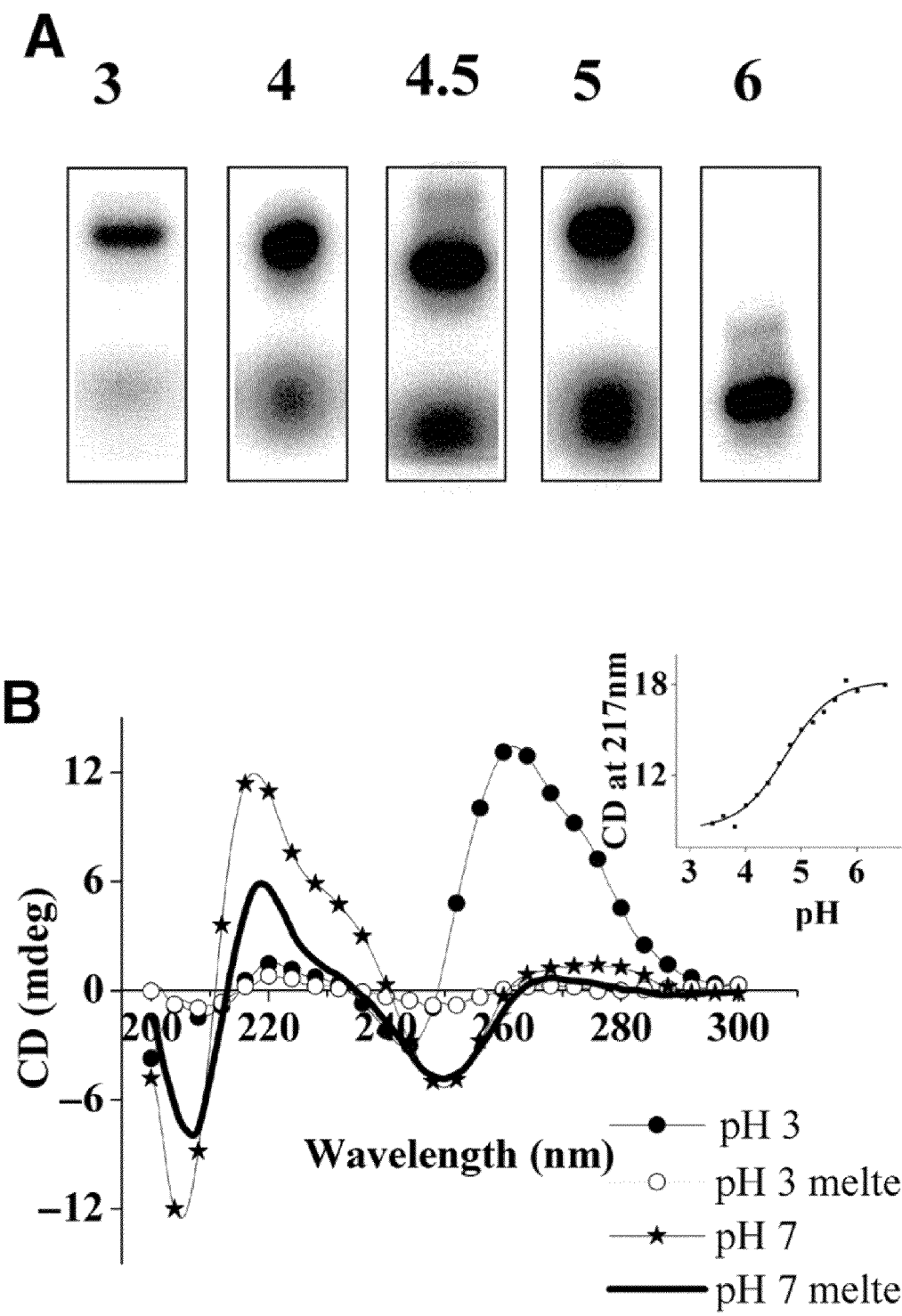
FIG. 1A is an illustrative gel electrophoresis of $dA_{15}$ showing two forms with different electrophoretic mobility.
FIG. 1B is an illustrative CD spectra of 1 µM $dA_{15}$ at pH 3.0 and pH 7.0 in 10 mM phosphate recorded at both 20° C. and 95° C. ($Na^+$=10 mM). Inset: CD at 217 nm of 5 µM $dA_{15}$ in 10 mM $Na^+$ cation as a function of buffer pH.

In the following detailed description, reference may be made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present technology is described herein using several definitions, as set forth throughout the specification. As used herein, unless otherwise stated, the singular forms "a," "an," and "the" include plural reference. Thus, for example, a reference to "an oligonucleotide" includes a plurality of oligonucleotide molecules, and a reference to "a nucleic acid" is a reference to one or more nucleic acids.

Nucleic acids, such as DNA and RNA, provide remarkable specificity and versatility in molecular recognition and are therefore excellent nanoscale building blocks to make precisely self assembled nanostructures. DNA nanomachines are synthetic DNA assemblies that switch between defined molecular conformations upon stimulation by external triggers. For example, DNA nanomachines are artificially designed assemblies that change their states in response to an input such as chemical stimuli generated by environmental cues. The present discovery includes an autonomous DNA nanomachine, which is responsive to a specific molecular trigger. The high-fidelity performance of DNA nanodevices illustrates the potential of DNA scaffolds responsive to more complex triggers in sensing, diagnostics and targeted therapies in living systems.

This disclosure describes a mechanism to hybridize two DNA strands together using a pH trigger. At acidic pH, certain A-rich sequences can hybridize by forming a parallel duplex. At neutral pH this mode of association is no longer operational and the two strands fall apart. This proves a mechanism to 'switch on and off' DNA base pairing using a pH trigger.

The present disclosure shows that at acidic pH, poly dA forms a parallel-stranded duplex. This is a new structural motif, referred to herein as the "A-motif." In some embodiments, a nucleic acid segment with A-motif forming capacity (such as $dA_{15}$) can undergo a pH-triggered conformational switch from a single helix at neutral pH to the A-motif at acidic pH with high efficiency and reversibility. The kinetics of association to form the parallel duplex is complete within millisecond time scale and represents the first observation of millisecond timescales in DNA-based molecular switches. Thus, A-motif forming sequences function as proton dependent molecular switches. The output of this molecular switch is mechanical motion associated with compression and extension between two well defined, helical, coiled states. The switching is two-state and is highly processive. While not wishing to be limited by theory, NMR evidence shows that the poly $dA_{15}$ duplex is held together by reverse Hoogsteen base-pairing between protonated adenosines, and molecular dynamics studies also shows electrostatic interactions between the phosphate backbone and N1-H⁺ of the base.

A-motif based pH switches have properties that make a valuable addition to the DNA nanotechnology toolkit. They have all the advantages of proton driven switches, being "clean", generating only water and salt as by-products for each cycle of switching. Thus, the switching is two-state and is highly processive. There is presently no switching mechanism in nucleic acids that is faster than this.

Structure of the Poly dA Oligonucleotides

In illustrative embodiments, the molecular switch has at least two A-motif forming sequences. As used herein, "nucleic acid," "nucleotide sequence," or "nucleic acid sequence" refer to a nucleotide, oligonucleotide, polynucleotide, or any fragment thereof and to naturally occurring or synthetic molecules, such as L-DNA, phosphorothioates, locked nucleic acids, etc.

As used herein, an "oligonucleotide" is understood to be a molecule that has a sequence of bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. A distinction may be made between oligodeoxyribonucleotides, which do not have a hydroxyl group at the 2' position, and oligoribonucleotides, which have a hydroxyl group in this position. Oligonucleotides also may include derivatives, in which the hydrogen of the hydroxyl group is replaced with organic groups, e.g., an allyl group. An oligonucleotide is a nucleic acid that includes at least two nucleotides.

One nucleic acid sequence may be "complementary" to a second nucleic acid sequence. As used herein, the terms "complementary" or "complementarity," when used in reference to nucleic acids (i.e., a sequence of nucleotides such as an oligonucleotide or a target nucleic acid), refer to sequences that are related by base-pairing rules. For natural bases, the base pairing rules are those developed by Watson and Crick. As an example, for the sequence "T-G-A", the complementary sequence is "A-C-T." Complementarity can be "partial," in which only some of the bases of the nucleic acids are matched according to the base pairing rules. Alternatively, there can be "complete" or "total" complementarity between the nucleic acids. The degree of complementarity between the nucleic acid strands has effects on the efficiency and strength of hybridization between the nucleic acid strands.

Oligonucleotides as described herein may be capable of forming hydrogen bonds with oligonucleotides having a complementary base sequence. These bases may include the natural bases such as A, G, C, T and U, as well as artificial bases. An oligonucleotide may include nucleotide substitutions. For example, an artificial or modified base may be used in place of a natural base such that the artificial base exhibits a specific interaction that is similar to the natural base.

An oligonucleotide that is complementary to another nucleic acid will "hybridize" to the nucleic acid under suitable conditions (described below). As used herein, "hybridization" or "hybridizing" refers to the process by which a oligonucleotide single strand anneals with a complementary strand through base pairing under defined hybridization conditions. "Specific hybridization" is an indication that two nucleic acid sequences share a high degree of complementarity. Specific hybridization complexes form under permissive annealing conditions and remain hybridized after any subsequent washing steps. "Hybridizing" sequences which bind under conditions of low stringency are those which bind under non-stringent conditions (6×SSC/50% formamide at room temperature) and remain bound when washed under conditions of low stringency (2×SSC, 42° C.). Hybridizing under high stringency refers to the above conditions in which washing is performed at 2×SSC, 65° C. (where SSC is 0.15M NaCl, 0.015M sodium citrate, pH 7.2).

In some embodiments, the poly dA sequences that make the molecular switch form one or more A-motifs. An "A-motif" is a nucleic acid (DNA and/or RNA) containing complex characterized by the presence of adenosine-rich stretches or stretches rich in adenosine derivatives, including two parallel-stranded duplexes in which the adenosine or derivatives thereof form a double helix. The complex may be synthesized from oligonucleotide sequences including a stretch of at least five, at least ten, at least fifteen, or at least twenty consecutive adenosines. Moreover, this motif may be formed by the interaction of stretches containing different numbers of adenosines. Furthermore, an adenosine-rich stretch may contain one or two non-adenosine base(s) in between the adenosines. However, this may reduce the stability of the A-motif. Although frame-shifted hybridizations could occur, these happen only in longer dA tracts, and can be avoided by employing shorter A-tracts that include, e.g., a CGA motif at either the 5' or 3' end to keep the strands in register. The adenosine stretches which comprise the A-motif may belong to different strands of nucleic acids; however, any two of them may also be linked together covalently or non-covalently. Also, any two of them may be part of a single nucleic acid strand wherein they are separated by a stretch of specified bases.

In some embodiments, the molecular switch includes at least two A-motif forming sequences on at least two separate oligonucleotides. The at least two oligonucleotides may each be at least 4, at least 8, at least 12, at least 16, at least 20, or at least 30 nucleotides in length. In illustrative embodiments, the at least two oligonucleotides may each be no more than about 50 nucleotides in length. In one embodiment, the at least two oligonucleotides, which interact to form the A-motif, may be partially complementary to a third oligonucleotide, which binds the at least two oligonucleotides for the formation of larger molecular assemblies.

In some embodiments, the molecular switch includes at least two A-motif forming sequences on a single oligonucleotide. The at least two A-motif forming sequences are spatially separated on the single oligonucleotide, such that they can interact to form an A-motif under the appropriate pH conditions. Interacting labels at or near the opposite ends of the oligonucleotide are brought into proximity, which results in a signal. In order to maintain the separation of the A-motif forming sequences, the single oligonucleotide may be partially complementary to another oligonucleotide. In this way, the A-motif forming oligonucleotide is partnered with another strand that is capable of dissociating when the A-motif is formed. For example, the partner strand may dissociate from the A-motif forming oligonucleotide at high pH due to inherent instability in the duplex. In some embodiments, the duplex is unstable due to the presence of one or more mismatches between the partner strand and the A-motif-forming oligonucleotide.

Minor modifications of the oligonucleotides may result in molecular switches which have substantially equivalent or improved activity as compared to the unmodified counterpart oligonucleotides. Such modifications may be deliberate, as by site-directed mutagenesis, or may be spontaneous. All of the oligonucleotides produced by these modifications are included herein as long as the pH-dependent conformational change still exists.

In some embodiments, the molecular switch includes at least one modified base, for instance natural modified bases or unnatural modified bases (or analogs of bases such as universal bases (such as nebularin, nitroindole or nitropyrrole derivatives). Adjusting the sequence of the oligonucleotides in the A-motif to include at least one modified base may alter the response time of the A-motif or alter the pH range at which the A-motif operates.

In an illustrative embodiment, the molecular switch includes two poly dA-containing oligonucleotides, each of which are capable of interacting and forming an A-motif. Each of the nucleotides may be about 20-50 nucleotides, about 25-45, about 30-45 or about 30-40 nucleotides in length. For example, the sequences of the oligonucleotides forming the A-motif of FIG. 2A, may include those shown in Table 1. Under certain pH conditions, such as acidic conditions, the A-motif forming sequences interact to form an A-motif.

In some embodiments, the poly dA-containing oligonucleotides include interacting labels that are brought into proximity at low pH, which results in a signal. The presence, absence, or magnitude of the signal may then be correlated to pH using known standards. Alternatively, a change in pH may be monitored in real-time.

Labels

In accordance with the methods and compositions disclosed herein, the oligonucleotides may include one or more labels. Oligonucleotides can be labeled by incorporating moieties detectable by one or more means including, but not limited to, spectroscopic, photochemical, biochemical, immunochemical, or chemical assays. The method of linking or conjugating the label to the nucleotide or oligonucleotide depends on the type of label(s) used and the position of the label on the nucleotide or oligonucleotide.

As used herein, "labels" are chemical or biochemical moieties useful for labeling a nucleic acid. "Labels" include fluorescent agents, chemiluminescent agents, chromogenic agents, quenching agents, radionucleotides, enzymes, substrates, cofactors, inhibitors, nanoparticles, magnetic particles, and other moieties known in the art. Labels are capable of generating a measurable signal and may be covalently or noncovalently joined to an oligonucleotide or nucleotide.

In illustrative embodiments, the oligonucleotides may be labeled with a "fluorescent dye" or a "fluorophore." As used herein, a "fluorescent dye" or a "fluorophore" is a chemical group that can be excited by light to emit fluorescence. Some fluorophores may be excited by light to emit phosphorescence. Dyes may include acceptor dyes that are capable of quenching a fluorescent signal from a fluorescent donor dye. Dyes that may be used in the disclosed methods include, but are not limited to, the following dyes and/or dyes sold under the following trade names: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-Hydroxy Tryptamine (HAT); 5-ROX (carboxy-X-rhodamine); 6-Carboxyrhodamine 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Cascade Blue™; Cascade Yellow; Catecholamine; CCF2 (GeneBlazer); CFDA; CFP—Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.18; Cy3.5™; Cy3™; Cy5.18; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); Flazo Orange; Fluo-3; Fluo-4; Fluorescein (FITC); Fluorescein Diacetate; FluoroEmerald; Fluoro-Gold (Hydroxystilbamidine); Fluor-Ruby; FluorX; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; NED™; Nitrobenzoxadidole; Noradrenaline; Nuclear Fast Red; Nuclear Yellow; Nylosan Brilliant Iavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; TET™; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; VIC®; wt GFP; WW 781; X-Rhodamine; XRITC; Xylene Orange; Y66F; Y66H; Y66W; Yellow GFP; YFP; YO-PRO-1; YO-PRO-3; YOYO-1; YOYO-3; and salts thereof.

Fluorescent dyes or fluorophores may include derivatives that have been modified to facilitate conjugation to another reactive molecule. As such, fluorescent dyes or fluorophores may include amine-reactive derivatives such as isothiocyanate derivatives and/or succinimidyl ester derivatives of the fluorophore.

The oligonucleotides and nucleotides of the disclosed compositions and methods may be labeled with a quencher. Quenching may include dynamic quenching (e.g., by FRET), static quenching, or both. Illustrative quenchers may include Dabcyl. Illustrative quenchers may also include dark quenchers, which may include black hole quenchers sold under the tradename "BHQ" (e.g., BHQ-0, BHQ-1, BHQ-2, and BHQ-3, Biosearch Technologies, Novato, Calif.). Dark quenchers also may include quenchers sold under the tradename "QXL™" (Anaspec, San Jose, Calif.). Dark quenchers also may include DNP-type non-fluorophores that include a 2,4-dinitrophenyl group.

In some situations, it may be useful to include interactive labels on two or more oligonucleotides with due consideration given for maintaining an appropriate spacing of the labels on the oligonucleotides to permit the separation of the labels during a conformational change in the A-motif. One type of interactive label pair is a quencher-dye pair, which may include a fluorophore and a quencher. The ordinarily skilled artisan can select a suitable quencher moiety that will quench the emission of the particular fluorophore. In an illustrative embodiment, the Dabcyl quencher absorbs the emission of fluorescence from the fluorophore moiety.

Alternatively, the proximity of the two labels can be detected using fluorescence resonance energy transfer (FRET) or fluorescence polarization. FRET is a distance-dependent interaction between the electronic excited states of two dye molecules in which excitation is transferred from a donor molecule to an acceptor molecule without emission of a photon. Examples of donor/acceptor dye pairs for FRET are known in the art and may include fluorophores and quenchers described herein such as Fluorescein/Tetramethylrhodamine, IAEDANS/Fluorescein (Molecular Probes, Eugene, Oreg.), EDANS/Dabcyl, Fluorescein/Fluorescein (Molecular Probes, Eugene, Oreg.), BODIPY FL/BODIPY FL (Molecular Probes, Eugene, Oreg.), BODIPY TMR/ALEXA 647, ALEXA-488/ALEXA-647, and Fluorescein/QSY7™.

The labels can be conjugated to the oligonucleotides directly or indirectly by a variety of techniques. Depending upon the precise type of label used, the label can be located at the 5' or 3' end of the oligonucleotide, located internally in the oligonucleotide's nucleotide sequence, or attached to spacer arms extending from the oligonucleotide and having various sizes and compositions to facilitate signal interactions. Using commercially available phosphoramidite reagents, one can produce oligonucleotides containing functional groups (e.g., thiols or primary amines) at either terminus, for example by the coupling of a phosphoramidite dye to the 5' hydroxyl of the 5' base by the formation of a phosphate bond, or internally, via an appropriately protected phosphoramidite.

Oligonucleotides may also incorporate oligonucleotide functionalizing reagents having one or more sulfhydryl, amino or hydroxyl moieties into the oligonucleotide sequence. For example, 5' phosphate group can be incorporated as a radioisotope by using polynucleotide kinase and [$\gamma^{32}$P]ATP to provide a reporter group. Biotin can be added to the 5' end by reacting an aminothymidine residue, introduced during synthesis, with an N-hydroxysuccinimide ester of biotin. Labels at the 3' terminus, for example, can employ polynucleotide terminal transferase to add the desired moiety, such as for example, cordycepin, $^{35}$S-dATP, and biotinylated dUTP. Oligonucleotide derivatives are also available as labels. For example, etheno-dA and etheno-A are known fluorescent adenine nucleotides which can be incorporated into the A-motif forming nucleic acids. Similarly, etheno-dC is another analog that can be used in A-motif forming nucleic acid synthesis.

Use of the A-Motif in DNA Nanoscale Assemblies

In accordance with one aspect, the A motif may be incorporated into nanoscale DNA architectures that can self-assemble and dis-assemble on externally added pH cues. These nucleic acid molecules may be used to create novel materials. This new non B-DNA based building block could have several applications in the dynamic assembly area of structural DNA nanotechnology. Apart from its high stability, the A-motif based switches are simple to construct, composed of just one type of DNA base, thus minimizing interference upon its incorporation as part of a larger DNA assembly. Because it is a non Watson-Crick based building block, it can be integrated into Watson-Crick base paired assemblies to realize switches with more complex functionalities. The A-motif represents a new mechanism by which two DNA strands may associate and dissociate triggered by pH. This will find application as a powerful method to site-specifically and reversibly glue pre-structured DNA assemblies together on providing a pH cue. For instance, by replacing a critically positioned Watson-Crick base-pairing site on a given DNA assembly by an A-motif forming sequence, it will transform that site into a sticky or non-sticky state on the application of an external pH stimulus. Thus, with the poly dA motif, one can build pH responsive 1D, 2D and 3D architectures because (i) the base-pairing here requires only two strands, (ii) directionality is conferred by the parallel stranded nature of the motif (as opposed to antiparallel B-DNA) and (iii) this mechanism is compatible with and does not interfere with Watson-Crick base pairing in an assembly. pH switchable 1D, 2D and 3D assemblies can have applications in DNA based computation strategies where they can act as logic gates.

In some embodiments, the A-motif may be used as a building block for DNA-materials and can be incorporated into larger DNA assemblies. A "DNA assembly" is a structure including at least one A-motif associated with other nucleic acid materials to produce a 2- and 3-dimensional structure. The DNA assembly can be formed by hybridization of the poly dA-containing nucleic acids. A DNA assembly may be synthesized following a divergent strategy (growing outwardly from an inner core). A DNA assembly may be synthesized following a convergent strategy (growing inwardly from the outside).

In some embodiments, the DNA assemblies are polynucleic acids that are assembled from repeating units (polygons, branched multimers, etc.) composed at least partially of A-motif forming nucleic acids. In an illustrative embodiment, the polygonal units are self-assembled, which self assembly involves synthesizing single stranded polynucleotides, each being designed to be self-complementary and/or complementary to another single stranded polynucleotide so as to be able to self anneal into a polygonal unit. The polygonal units have single-stranded poly dA overhangs. The polygonal units may then be assembled into larger structures in response to a pH cue because these repeating units hybridize to form an A-motif, thereby forming more complex polynucleic acid structures having two dimensional or three dimensional periodic lattices with symmetrical intermolecular contacts.

Figure 21:
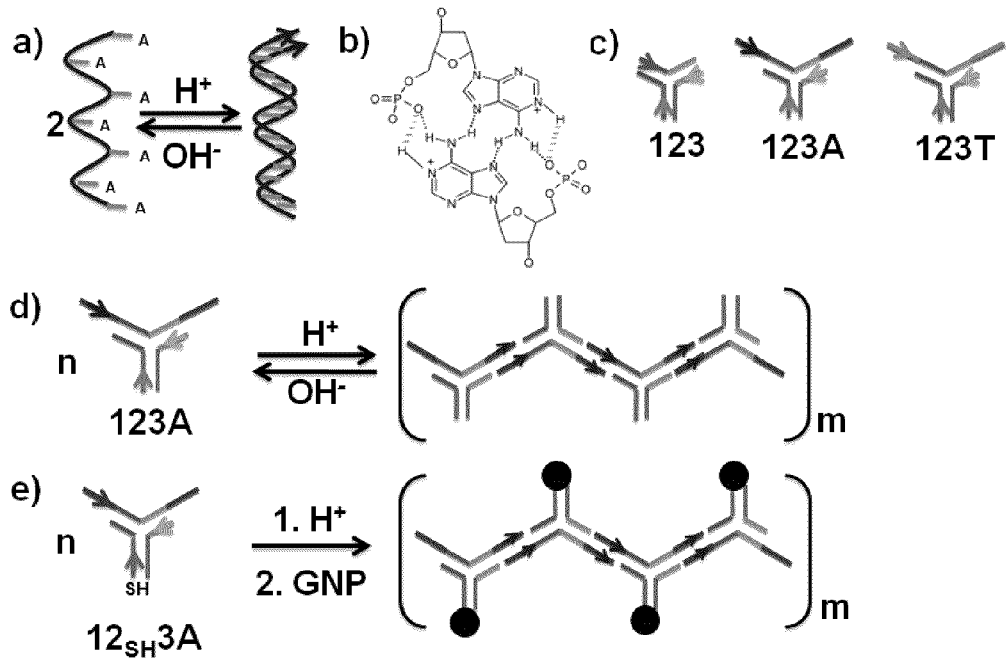
FIG. 21 illustrates a strategy for the construction of pH reversible 1D DNA architecture. (a) Mechanism of A-motif formation. (b) Base pairing in A-motif interaction. c) Building blocks used in present study; 123: 3WJ without AFOs, 123A: 3WJ with AFOs, 123T: 3WJ where AFOs are replaced by an equal number of thymines. (d) Reversible association of isolated building blocks 123A into 1D architecture via A-motif formation. (e) Arrangement of gold nanoparticles (GNP) on resultant 1D architecture formed from 12SH3A building block carrying a thiol modification.

In an illustrative embodiment, a DNA three way junction (3WJ) is synthetized which incorporates A-rich overhangs (123A) as shown in FIG. 21. These A-motif forming overhangs (AFOs) act as 'sticky ends' only at acidic pH. Therefore, at neutral pH, 123A would be expected to remain as a monomeric 3WJ. Upon lowering the environmental pH, the AFOs would be expected to hybridize into A-motifs and thus assemble 123A into an extended 1D DNA architecture. This embodiment shows the reversible assembly and complete disassembly of a defined 1D architecture into its building block. Both steps are controllable by a pH toggle that switches ON and OFF and unusual mode of DNA hybridization, namely A-motif formation.

Illustrative sequences of the oligonucleotides that may be used to form the three way junctions include: Oligo 3A: 5'-AAAAAAAAAA AAAAAACATG CCGGTATTT AAAGCCTTTC GAAGATATCG TGGTTCGAGA AAAAAAAAAA AAAAA-3' (SEQ ID NO: 5); Oligo 2: 5'-CGAGCTGCAG CAGCTGTTAT TTAGGCTTTA AATACCGGCA TG-3' (SEQ ID NO: 6); Oligo 1: 5'-CTCGAACCAC GATATCTTCG TTATAACAGC TGCTG-CAGC TCG-3' (SEQ ID NO: 7); Oligo 3: 5'-ATGCCGGTAT TTAAAGCCT TTCGAAGATA TCGTGGTTCG AG-3' (SEQ ID NO: 8); Oligo 3T: 5'-TTTTTTTTTT TTTTTTCATG CCGGTATTTA AAGCCTTTCG AAGATATCG TGGTTCGAG TTTTTTTTT TTTTTTT-3' (SEQ ID NO: 9).

Complex building blocks may be oligomerized by A-motif formation with as much fidelity as seen in Watson Crick hybridization. The sequence of AFOs is simple, non-interfering and thus can be easily integrated into precharacterized B-DNA based tiles. Thus, this method can be used to make pH toggled 2D and 3D rigid scaffolds that may be reversibly assembled by controlling pH. Given the advantages of the non-toxic working cycle of the A-motif and its integratability to B-DNA based hybridization assemblies, DNA walkers incorporating A-motif based feet could increase processivity as well as directionality of walkers that currently use only B-DNA based feet A-motif formation could aid movement using a chemical fuel without affecting the track, thus increasing processivity. Thus, a combination of B-DNA and A-motif forming sequences can be used to achieve greater control of nanoscale movement of DNA devices in terms of directionality and processivity.

3D DNA polyhedra are also promising as targettable drug delivery agents. Incorporation of A-motifs overhangs in these structures will lead to polyhedra that can be disrupted on a pH cue to release a payload. Polyhedra made to date suffer from the fact that their disassembly is not reversible as they are made of B-DNA building blocks. The application of such a nanorobotic device (the A-motif) could be to restrict the transport of material in or out of the nanocontainers in a controlled fashion. Thus, the A-motif has the potential to both sense and act, for example by combining a diagnostic sensor of complex signals with the controlled release of, or access to, a payload.

In some embodiments, the DNA assemblies may have one or more molecules attached thereto. Such pendant materials include, but are not limited to, nanoparticles, small molecules, catalysts, enzymes, peptides and other proteins, or other nucleic acids, e.g., ribozymes.

Use of the A-Motif as a pH Sensor

Adenine has a pKa of 3.6 which is suitable for sensing pH in the range from 4.5 to 5.5. Thus A-motif based nanomachines can be used to measure pH in late endosomes or lysosomes. Measurement of pH inside lysosomes is very important given that in certain kind of life threatening disease like lysosomal storage disorder there is marked change in pH which can be used to diagnose the disease. Thus A-motif based switches can be used as diagnostic tool in those cases. Moreover, A-motif based switches can be made genetically encodable because natural abundance adenosines in poly A tail of mRNAs. All the required enzymes to polyadenylate are present in cell so by careful design of sequences with required polyadenylation signals, genetically encodable RNA based switches can be made.

Introducing the Poly dA Oligonucleotides Into Cells

In some embodiments, the sample in which pH is to be measured can be a biological sample, e.g., a biological tissue or a cell or an organism. The method is suitable for measuring pH in a specific region of the cell, e.g., the cytosol, or an organellar space such as, but not limited to, the inner mitochondrial matrix, the lumen of the Golgi, the endoplasmic reticulum, the chloroplast lumen, the lumen of a lysosome, the nucleus, or the lumen of an endosome.

The A-motif forming oligonucleotides can be readily introduced into a host cell, e.g., mammalian (optionally human), bacterial, parasite, yeast or insect cell by any method in the art. For example, A-motif forming oligonucleotides can be transferred into a host cell by physical, chemical or biological means. It is readily understood that the introduction of the oligonucleotides yields a cell in which the intracellular pH may be monitored. Thus, the method can be used to measure intracellular pH in cells cultured in vitro. The A-motif forming oligonucleotides can also be readily introduced into a whole organism to measure the pH in a cell or tissue in vivo. For example, A-motif forming oligonucleotides can be transferred into an organism by physical, chemical or biological means, e.g., direct injection.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (Molecular Cloning: A Laboratory Manual, Cold Spring Harbor Laboratory, New York, 2001), and in Ausubel et al. (Current Protocols in Molecular Biology, John Wiley & Sons, New York, 1997).

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. One colloidal system for use as a delivery vehicle in vitro and in vivo is a liposome (i.e., an artificial membrane vesicle). The preparation and use of such systems is well known in the art.

In some embodiments, the use of lipid formulations is contemplated for the introduction of the A-motif into host cells (in vitro, ex vivo or in vivo). In a specific embodiment, the A-motif may be associated with a lipid. The A-motif forming oligonucleotides associated with a lipid may be encapsulated in the aqueous interior of a liposome, interspersed within the lipid bilayer of a liposome, attached to a liposome via a linking molecule that is associated with both the liposome and the oligonucleotide(s), entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid, lipid/oligonucleotide compositions are not limited to any particular structure in solution. For example, they may be present in a bilayer structure, as micelles, or with a "collapsed" structure. They may also simply be interspersed in a solution, possibly forming aggregates which are not uniform in either size or shape.

Liposome-mediated oligonucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments, the lipid may be associated with a hemagglutinating virus (HVJ). This has been shown to facilitate fusion with the cell membrane and promote cell entry of liposome-encapsulated DNA. In other embodiments, the lipid may be complexed or employed in conjunction with nuclear non-histone chromosomal proteins (HMG-1). In yet further embodiments, the lipid may be complexed or employed in conjunction with both HVJ and HMG-1.

In some embodiments, the one or more A-motifs are linked to a targeting sequence that directs the A-motif forming oligonucleotides to a desired cellular compartment. Examples of targeting sequences include, but are not limited to, the amino terminal 81 amino acids of human type II membrane-anchored protein galactosyltransferase for directing the fluorescent indicator protein to the Golgi and the amino terminal 12 amino acids of the presequence of subunit IV of cytochrome c oxidase for directing the A-motif forming nucleic acids to the mitochondrial matrix. The 12 amino acids of the presequence of subunit IV of cytochrome c oxidase may be linked to the A-motif forming nucleic acids through a linker sequence.

In Vivo/Ex Vivo Detection of pH in Cells or Tissues Using the A-Motif

Figure 5:
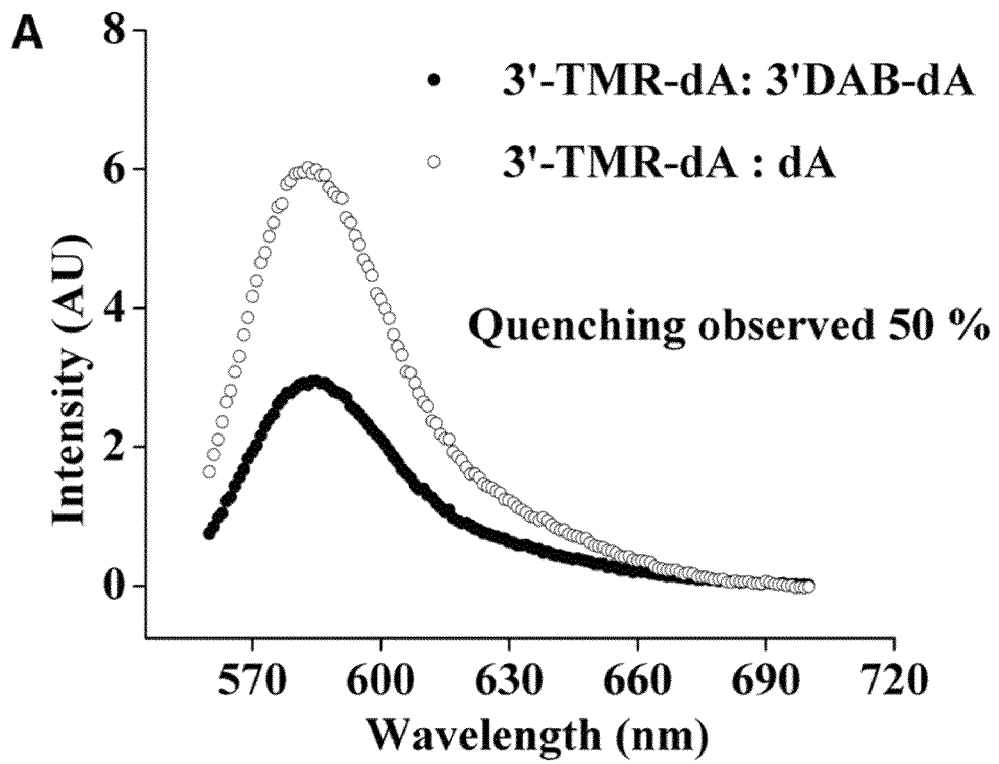
FIG. 5A is a graph of an illustrative fluorescence quenching experiment on the dual labeled poly $dA_{15}$ duplex of 1:50 3'-TMR-$dA_{15}$:3'-Dabcyl-$dA_{15}$ (filled circles) and 1:50 3'-TMR-$dA_{15}$: 3'-unlabeled $dA_{15}$ (open circles) at 100 nM TMR-$dA_{15}$ in 30 mM Na-phosphate buffer, pH 3 ($Na^+$=30 mM).
FIG. 5B is an graph of UV thermal melting of $dA_{15}$ duplex at 10 mM buffer, pH 3 ($Na^+$=10 mM). Inset: CD spectra of 5 µM $dA_{15}$ at 0 mM, 15 mM, 30 mM, 75 mM, 150 mM, 200 mM and 250 mM NaCl solution, pH 3.
Figure 5:
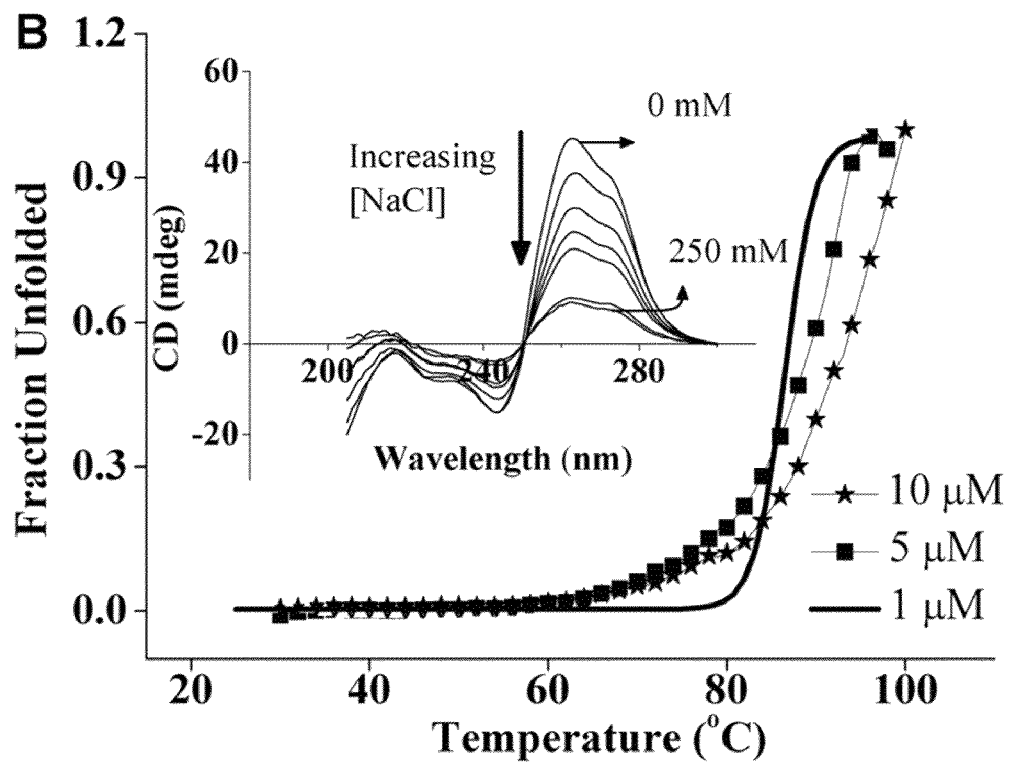

In some embodiments, the methods provide for determining the pH of a sample by contacting the sample with an indicator including one or more A-motifs whose emission intensity changes as pH varies between pH 4 and 10 or between pH 5 and 7, and exciting the indicator, and then determining the intensity of light emitted by the one or more A-motifs at a one or more wavelengths. The emission intensity or signal magnitude of one or more A-motifs indicates the pH of the sample. In an illustrative embodiment, the one or more A-motifs can be a combination of oligonucleotides similar to the one shown in FIG. 5.

In illustrative embodiments, the A-motifs may be used to monitor the pH changes in real-time during cellular processes. In one embodiment, the A-motifs is used to monitor endocytosis. While not wishing to be limited by theory, acidification plays a major role in facilitating cargo dissociation from receptors or in mediating cellular entry of toxins and viruses during endocytosis. As demonstrated in the Examples, the A-motif exhibits a pH response inside cells illustrated by the capture of spatiotemporal pH changes associated with endocytosis in living cells.

Fluorescence in the sample can be measured in a variety of ways, such as using a fluorometer or fluorescence microscopy. In general, excitation radiation, from an excitation source having a first wavelength, passes through excitation optics. The excitation optics cause the excitation radiation to excite the sample. In response, labels associated with the one or more A-motifs in the sample emit radiation which has a wavelength that is different from the excitation wavelength. Collection optics then collect the emission from the sample. The device can include a temperature controller to maintain the sample at a specific temperature while it is being scanned. If desired, a multi-axis translation stage can be used to move a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

In one embodiment, the detecting includes measuring the magnitude of the signal generated, wherein the magnitude indicates the pH of the cell or region thereof. In one embodiment, wherein the magnitude of the signal changes as the pH varies from pH 5 to 10 or pH 5 to 7. For FRET, the emission from the acceptor fluorophore increases as the A-motif forms a double helix, i.e., as the A-motif is formed when the pH decreases. Likewise, the emission from the acceptor fluorophore decreases as the A-motif assumes an open state, i.e., as the A-motif dissociates when the pH increases. For fluorescence quenching, the emission from the fluorophore decreases as the A-motif forms a double helix, i.e., as the A-motif is formed when the pH decreases. Likewise, the emission from the fluorophore increases as the A-motif forms an open state, i.e., as the A-motif dissociates when the pH increases.

As used herein, an "increase" (or "decrease") in a signal from the labeled A-motif refers to the change in a signal in the sample compared to a reference sample. The reference sample may be a control sample (e.g., an untreated population of cells where the effects of a drug or agent are being exampled), or it may be the same sample at a different period of time, for instance, where the intracellular pH is being monitored to follow one or more cellular processes.

As used herein, the term "detectable" refers to a property of the labeled A-motif that allows one to determine the pH of a sample by detecting activity, e.g., fluorescence activity, possessed by the A-motif under certain pH conditions. In some embodiments, the signal from the A-motif is normalized by plotting the donor/acceptor (D/A) signal ratio as a function of pH in a standard reference sample. pH variation on a doubly-labeled A-motif changes the ratio between its closed and open states thereby resulting in different ratios of the donor and acceptor intensities (D/A) because of FRET in the closed state due to A-motif formation.

In one embodiment, a pH calibration curve may be generated to which test samples may be compared and normalized. An intracellular calibration curve may be generated as described in the Examples. Briefly, cells are pulsed, washed, incubated with an ionophore in buffers at a given pH and then mildly fixed. Donor and acceptor FRET images are acquired from which D/A ratios are obtained. The mean D/A of individual cells or regions thereof at each pH are plotted as a function of pH for the intracellular pH calibration curve. The D/A ratio of the test sample can be compared to the calibration curve.

In one embodiment, intracellular pH may be monitored for the purposes of examining cellular phenomena and/or screening the effects of various compounds, wherein the level of the signal from an A-motif (e.g., increased or decreased signal) in a test sample at a first time point is determined and compared with the level found in a test sample obtained at a later time point. The change in signal may reflect a relative change in pH between the two samples. For example, where a FRET pair is used as a label, an increase in signal from one time point to another may indicate an increase in pH between the two time points. Likewise, a decrease in signal from one point to another may indicate a decrease in pH. The absolute level of signal may be compared to a reference sample of known standards or reference samples in order to determine the precise pH of the sample. The sample can be classified or assigned to a particular pH value based on how similar the measured levels were compared to the control levels for a given group.

As one of skill in the art will understand, there will be a certain degree of uncertainty involved in making this determination. Therefore, the standard deviations of the control or reference group levels can be used to make a probabilistic determination and the method of this disclosure are applicable over a wide range of probability-based determinations. Thus, for example, and not by way of limitation, in one embodiment, if the measured level of signal falls within 2.5 standard deviations of the mean of any of the control or reference groups, then that sample may be assigned to that group. In another embodiment if the measured level of signal falls within 2.0 standard deviations of the mean of any of the control or reference groups then that sample may be assigned to that group. In still another embodiment, if the measured level of signal falls within 1.5 standard deviations of the mean of any of the control or reference groups then that sample may be assigned to that group. In yet another embodiment, if the measured level of signal is 1.0 or less standard deviations of the mean of any of the control or reference groups levels then that sample may be assigned to that group. Thus, this process allows determination, with various degrees of probability, in which group a specific sample should be placed.

Statistical methods can also be used to set thresholds for determining when the signal intensity in a test sample can be considered to be different than or similar to the reference level. In addition, statistics can be used to determine the validity of the difference or similarity observed between a test sample's signal intensity and the reference level. Useful statistical analysis methods are described in L. D. Fisher & G. vanBelle, *Biostatistics: A Methodology for the Health Sciences* (Wiley-Interscience, NY, 1993). For instance, confidence ("p") values can be calculated using an unpaired 2-tailed t test, with a difference between groups deemed significant if the p value is less than or equal to 0.05.

The A-motif pH sensors have may vary in their respective $pK_a$, and the differences in $pK_a$ can be used to select the most suitable A-motif sensor for a particular application. In general, a sensor should be used whose $pK_a$ is close to the pH of the sample to be measured. For example, the $pK_a$ may be within 1.5 pH unit, within 1.0 pH unit, or within 0.5 pH units of the sample. The $pK_a$ of the A-motif may be changed by, e.g., adjusting the number of adenosine residues in the A-motif or introducing chemical derivatives of adenosine.

To minimize artefactually low fluorescence measurements that occur due to cell movement or focusing, the fluorescence of the A-motif can be compared to the fluorescence of a second sensor, e.g., a second A-motif that is also present in the measured sample. The second A-motif should have an emission spectra distinct from the first A-motif so that the emission spectra of the two sensors can be distinguished. Because experimental conditions such as focusing and cell movement will affect fluorescence of the second sensor as well as the first sensor, comparing the relative fluorescence of the two sensors may allow for the normalization of fluorescence. A convenient method of comparing the samples is to compute the ratio of the fluorescence of the first fluorescent protein pH sensor to that of the second fluorescent protein pH sensor.

In one embodiment, circular dichroism spectroscopy may be used to detect changes in the secondary structure of the A-motif in response to changes in pH. Circular Dichroism (CD) is observed when optically active matter absorbs left and right hand circular polarized light slightly differently. It is measured with a CD spectropolarimeter. In another embodiment, change in intracellular pH may be detected by observing Raman band changes in the A-motif. In this embodiment, the A-motif contains a gold nanoparticle label and a Raman tag. The Raman band changes may be detected when the gold nanoparticle is brought close to a Raman tag.

Kits

The materials and components described for use in the methods may be suited for the preparation of a kit. Thus, the disclosure provides a detection kit useful for determining the pH of sample, including, but not limited to a cell or region thereof. Specifically, the technology encompasses kits for measuring the pH of one or more cells in a sample. For example, the kit can comprise labeled poly dA nucleic acids capable of detecting the pH of a cell or region thereof.

In one embodiment, the methods described herein may be performed by utilizing pre-packaged diagnostic kits comprising the necessary reagents to perform any of the methods of the technology. For example, such a kit would include a detection reagent for measuring the pH of a cell or region thereof. In one embodiment of such a kit, the detection reagents are an A-motif, such as that shown in FIG. 5 and defined by the sequences in Table 1. Oligonucleotides are easily synthesized and are stable in various formulations for long periods of time, particularly when lyophilized or otherwise dried to a powder form. In this form, they are easily reconstituted for use by those of skill in the art. Other reagents and consumables required for using the kit could be easily identified and procured by those of skill in the art who wish to use the kit. The kits can also include buffers useful in the methods of the technology. The kits may contain instructions for the use of the reagents and interpreting the results.

In another embodiment, the technology provides a kit comprising at least one sample (e.g., a pH standard) packaged in one or more vials for use as a control. Each component of the kit can be enclosed within an individual container and all of the various containers can be within a single package, along with instructions for interpreting the results of the assays performed using the kit.

EXAMPLES

The present compositions, methods and kits, thus generally described, will be understood more readily by reference to the following examples, which are provided by way of illustration and are not intended to be limiting of the present methods and kits. The following is a description of the materials and experimental procedures used in the Examples.

Example 1

Characterization of a Poly dA Molecular Switch

In this example, the structure of a poly dA-based molecular switch was characterized. A segment of poly dA 15 nucleotides long was chosen because this is within the limits of the observed persistence length of the poly dA single helix. Using gel electrophoresis, circular dichroism (CD) spectroscopy and concentration dependent thermal melts, we showed that poly $dA_{15}$ existed in two different structural forms at acidic pH and neutral pH. 1D $^1$H NMR studies on a short homopolymeric deoxyadenosine sequence such as $dTA_6$ at both pH values showed that the acidic form of short homopolymeric deoxyadenosines was a parallel duplex. The relative strand polarity in the $dA_{15}$ duplex was also confirmed independently by fluorescence quenching experiments. In order to delineate the molecular basis of duplex formation by such poly dA sequences, the mode of base-pairing in $dTA_6$ was established by 2D NMR, which revealed that the duplex was held by reverse Hoogsteen type $AH^+$—$H^+A$ base pairs. We also present an atomistic model of the $dA_{15}$ parallel duplex by molecular dynamics simulation. Importantly, we show that poly dA sequences such as $dA_{15}$ undergo a pH-induced conformational transition from the single helical form to the right-handed symmetric parallel-stranded duplex form in a highly reversible manner. The kinetics of this association was found to occur on millisecond time scales. This fast association time scale makes it an ideal system for use as a molecular nanoswitch in structural DNA nanotechnology.

Sample preparation. Desalted $dA_{15}$, $dTA_6$ and HPLC purified 5'-TAMRA as well as 3'-TMR (attached via a $C_3$ linker) labeled $dA_{15}$ were obtained from Bioserve India. HPLC purified 3'-DABCYL labeled $dA_{15}$ was obtained from Ocimum Biosolutions, India and used without further purification. Samples were prepared in buffer of desired pH by incubating them at 4° C. for 12 h prior to measurement. Heating was avoided to decrease the pH-induced depurination.

Native gel electrophoresis. $dA_{15}$ was phosphorylated at 5' end with $P^{32}$ by T4 PNK forward reaction and γ-$P^{32}$ labeled ATP. Labeled DNA was doped with unlabeled $dA_{15}$. The labeled and unlabeled $dA_{15}$ mixture was incubated at different pH in 2 μM and then electrophoresed in 15% polyacrylamide gel buffered at different pH with Robinson Britton Buffer [($CH_3COOH$)=($H_3PO_4$)=($H_3BO_3$)=0.04 M; pH adjusted with NaOH] at 10 V/cm for 3 h. The gels were dried in slab gel drier and exposed to Fujifilm BAS-IP MS 2025 imaging plate and plates were imaged in Fujifilm FLA-2000 phosphoraimager.

CD spectroscopy. All the CD experiments were done using a Jasco J-815 CD spectropolarimeter equipped with Peltier temperature controller. All the data were collected from 300 to 200 nm at a scan rate of 50 nm/min at 0.2 nm data intervals and are presented as an average of three successive scans unless specified. Samples were made at desired concentrations in phosphate buffer at pH 3 and 7 with desired ionic strength. For acidic pH, we used $NaH_2PO_4$/$H_3PO_4$ buffer and at neutral pH, $Na_2HPO_4$/$NaH_2PO_4$ buffer. Samples were annealed as described before. pH titrations were done using 0.01 N HCl or 0.01 N NaOH. Samples were used only once. Reproducibility was ensured on multiple samples prepared similarly.

Fluorescence spectroscopy. Fluorescence experiments were done on a JASCO J-815 CD Spectropolarimeter equipped with fluorescence detector or on FLUOROLOG-SPEX spectrofluorimeter using either 520 or 550 nm excitation wavelength and emission spectra were recorded from 540/560 to 700 nm. Emission spectra, presented as an average of two successive scans. Kinetics of association and dissociation of poly dA was done using a custom built single molecule tracking (Olympus IX 70) inverted microscope equipped with photon counting APD. pH jumps were performed by addition of desired strong buffer to a weakly buffered solution of 5'-TAMRA-$dA_{15}$. For distance calculation experiments, samples of 1:50 3'-TMR-$dA_{15}$: 3'-DABCYL-$dA_{15}$ or 1:50 3'-TMR-$dA_{15}$:$dA_{15}$ at 5 μM were used.

Molecular dynamics simulations. All the models of poly dA duplex and single strands are made using NAMOT 2 software and simulated using PMEMD (37) program of AMBER9 (38) software suite with all-atom AMBER03 force field. The equilibration protocols were followed as described previously (39,40). Structures were visualized by PyMOL and UCSF Chimera software (41,42).

NMR experiments. All NMR spectra were recorded on Bruker Avance-500 and −800 MHz spectrometer. A total of 1 mM strand concentration in 50 mM Na-acetate-d3 buffer at pH 4.0 was used to prepare samples for all 1D experiments. 10% $D_2O$ was added before taking the spectra. Whereas, for proton exchange experiments, samples in Na-acetate-d3 buffer was lyophilized overnight and reconstitute in $D_2O$. pH of this solution was adjusted to 4 by addition of 4-5 μl of DCl and incubated at 4° C. overnight. pH 8 spectra was taken after quickly elevating the pH by addition of 15 μl of 1 M NaOH to 500 μl sample. Water suppression was achieved using an excitation Sculpting solvent suppression programmed (43). For 1D experiment 1024 scans were taken, the spectral width was maintained at 10 KHz, the thymine methyl chemical shift at 1.8 δ ppm was used as the internal standard. For NOESY experiments, (512×2048) complex points were collected, a 2 kHz spectral width was employed in both dimensions with acquisition times of 0.3 s in $t_2$ and 0.3 s in $t_1$, using a 200 ms mixing time for seeing H1'-Adenine H8 and 100 ms for H2'/H2"-Adenine H8.

TABLE 1

Exemplary Poly dA Sequences

| Name | Sequence | SEQ ID NO: |
|---|---|---|
| Poly $dA_{15}$ | 5'-d(AAAAAAAAAAAAAAA)-3' | SEQ ID NO: 1 |
| $dTA_6$ | 5'-d(TAAAAAA)-3' | |
| 3'-Dabcyl-$dA_{15}$ | 5'-d(AAAAAAAAAAAAAAA)-Dabcyl-3' | SEQ ID NO: 2 |
| 3'-TMR-$dA_{15}$ | 5'-d(AAAAAAAAAAAAAAA)-TMR-3' | SEQ ID NO: 3 |
| 5'-TAMRA-$dA_{15}$ | 5'-TAMRA-d(AAAAAAAAAAAAAAA)-3' | SEQ ID NO: 4 |

Native PAGE evidences duplex formation. In order to see whether $dA_{15}$ could self associate like its RNA analogue at acidic pH, we analyzed its electrophoretic mobility at a range of pH values from pH 3 to pH 7 by native polyacrylamide gel electrophoresis (PAGE) (FIG. 1A). Samples of 2 μM 5' P-32 labeled $dA_{15}$ was equilibrated in phosphate buffer of the desired pH and electrophoresed on 15% native PAGE of the corresponding pH. At pH 3, $dA_{15}$ shows a band of lower mobility, which increasingly disproportionates into a band of higher mobility with progressively increasing pH (FIG. 1A). Thus, at pH 6 and above only a single band of higher mobility is observed. This clearly indicates that at acidic pH, $dA_{15}$ forms a secondary structure of lower mobility and above pH 6, adopts a structure of higher mobility, with both forms being differently populated at intermediate pH values. This suggests that $dA_{15}$ adopts two different forms at acidic and neutral pH values.

pH-induced structural change probed by CD spectroscopy. Having established that $dA_{15}$ exists in two differently migrating forms that are pH dependent, we analyzed these forms further using CD spectroscopy (FIG. 1B). Samples of 1 μM $dA_{15}$ were prepared at pH 3.0 and 7.0 as described above. At 20° C., $dA_{15}$ at pH 7.0 showed a characteristic CD trace with a strong positive maximum at 217 nm with a shoulder at 232 nm, a weak positive band at 275 nm and negative bands centered at 250 nm and 206 nm. This spectrum is characteristic of single-stranded poly dA which is well documented (44). Upon heating to 95° C., this trace changed to one where the maximum at 275 nm was abolished and the minimum at 206 nm shifted to 210 nm. The CD spectrum of 1 μM $dA_{15}$ at pH 3.0, on the other hand, was completely different from that at pH 7.0. At 20° C., the 217 nm positive band characteristic of the single helix was absent. Instead, only an intense, positive band maximum at 262 nm with a shoulder at 275 nm and a weak minimum at 245 nm was observed. On heating to 95° C., these bands completely disappear, flattening out to comparatively negligible CD characteristic of ssDNA. The structure of poly dA15 at acidic pH evidenced a thermal transition by CD as well as UV, where the stability of the structure was concentration dependent further supporting its intermolecular nature (see data below). Poly $dA_{15}$ at acidic pH, thus assumes a structure entirely different from the single-stranded helix, as seen clearly from their completely different CD signatures and melting behavior.

1D and 2D NMR establish structure of the duplex in solution. In order to get more structural detail on such short, homo A-tracts in DNA at acidic pH, high resolution NMR studies were performed on a truncated form of $dA_{15}$, desymmetrized by a thymine at the 5' end to enable complete assignment by NMR. We chose $dTA_6$ based on literature evidence that affirmed six adenines to be the minimum length that structurally and functionally represented the poly rA helix (45). One millimolar $dTA_6$ in 10% $D_2O/H_2O$ at 10° C. on a Bruker 800 MHz NMR spectrometer showed exactly six Adenine H8 protons and only one type of Thymine $CH_3$ and H6 protons (see FIG. 3A) confirming that this sequence forms a single population of dimer in bulk, precluding any slipped structures for at least six contiguous adenine tracts. Importantly, the 1D spectrum of $dTA_6$ showed hydrogen-bonded N6 aminos that were downfield shifted to 8.4-9 δppm from the usual 6-7 δppm for these protons (see FIG. 3A), characteristic of hydrogen bonding seen in A-A base pairing (FIG. 2B) (30). These were not seen in either the $D_2O$ exchanged spectrum at pH 4 or the single helical, monomeric structure at pH 8 in 5% $D_2O$ [FIG. 3A (2 and 3)]. Furthermore, these H-bonded amino protons also showed the characteristic dramatically reduced intensity observed for A-A base pairs bonded on their Hoogsteen faces (28-30) as indicated in Scheme 1B. Furthermore, 2D NOESY of $dTA_6$ showed a set of eleven H8-H1'NOEs (FIG. 3B) characteristic of six A-A base pairs found in A-containing duplexes that form a parallel-stranded Π-DNA helix (29). Importantly the absence of NOEs between Adenine $NH_2$ protons and the Adenine H2 protons are consistent with the reverse Hoogsteen base-pairing scheme seen in the dA containing parallel duplex (30).

Salt dependence studies. In order to investigate the effect of salt on the stability of the duplex, samples were made at 5 μM strand concentration in unbuffered solution, pH 3 and CD measured with incremental additions of NaCl. As evident from the CD profile in inset FIG. 5B, with increasing salt, the intensity at 262 nm which is a clear diagnostic of the duplex, decreases (see also FIG. 8). It can be seen that the signal decreases sharply and tapers off at ~250 mM NaCl. Such dependence has been observed also for the poly rA duplex which is stabilized by electrostatic interaction between $N1-H^+$ of adenosine and phosphate oxygen (17). That such dependence is recapitulated in the poly dA duplex indicates that such an electrostatic interaction is also present here, further supporting the base pairing mode observed by NMR.

Figure 4:
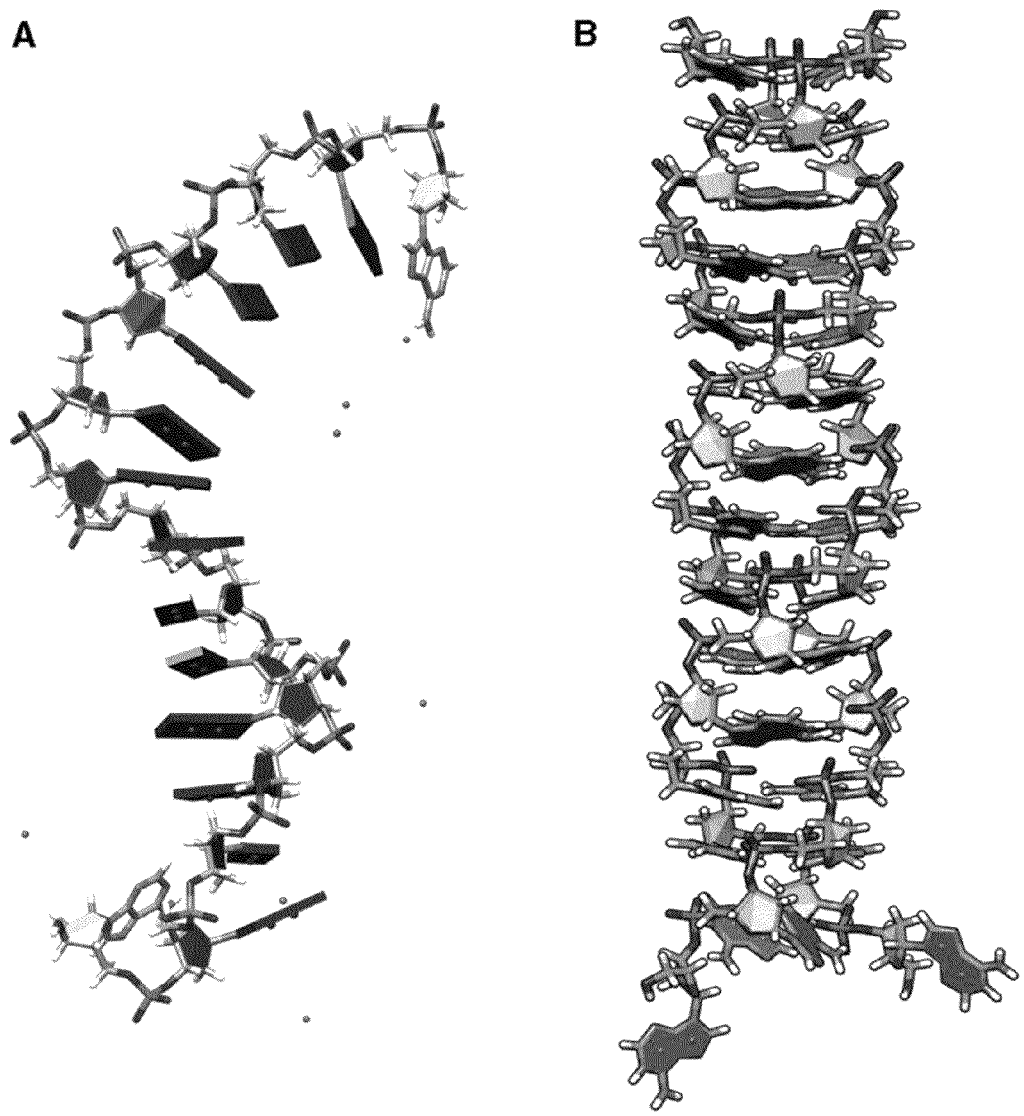
FIG. 4A is an illustrative equilibrium snapshot of the single-stranded $dA_{15}$ after 20 ns long MD simulation using AMBER revealing highly stacked adenine nucleobases.
FIG. 4B is an instantaneous snapshot of N1-protonated adenosine mediated parallel duplex of $dA_{15}$ after 20 ns long MD simulation revealing a Π-helical structure with tilted base.

Molecular dynamics (MD) study. MD simulations of the single-stranded unprotonated $dA_{15}$ indeed revealed a robust helical structure primarily driven by efficient stacking of the adenine nucleobases (FIG. 4A) (19). Importantly, MD simulations on the parallel-stranded N1 protonated poly $dA_{15}$ duplex yielded a structure which is similar to the Π-DNA helix (FIG. 4B) (29). The $AH^+$—$H^+A$ base pairs in this duplex adopted a 12° tilt from the horizontal to the helical axis. This tilting is characteristic of the $AH^+$—$H^+A$ base pairs previously described (17). Interestingly, MD also reveals an extra strong interaction resembling an H-bond of ~2.9 Å distance between the phosphate and the N1 protonated site on adenines shown in dashed line in FIG. 2B. If this is true it would imply almost six hydrogen bonds per $AH^+$—$H^+A$ base pair which is in line with UV melting studies and kinetics that evidence unusually high stability of the poly $dA_{15}$ duplex (data presented below).

Thermal stability studies. To investigate the thermal stability of $dA_{15}$, at both acidic and neutral pH, both samples were thermally denatured following the UV absorbance at 260 nm or CD at 262 nm. Two micromolar $dA_{15}$ at pH 7.0 evidences a weakly structured form as seen from the broad and noncooperative melt centered at 46° C. (see additional data below for details). This is in line with previous findings on single helices of poly dA that suggest that stacking interactions are probably the only stabilizing forces in the poly dA single helix (25). For the duplex melting, freshly prepared samples of $dA_{15}$ at pH 3.0 were used which evidenced a cooperative dissociation centered at ~80° C. at 1 μM $dA_{15}$ (see FIG. 5B). Melting temperature was found to vary with strand concentration indicating intermolecular nature of the $dA_{15}$-duplex. In all cases, regardless of strand concentration, the transitions were sharp, taking place over <12° C. as seen in well-formed B-DNA duplexes indicating that the $dA_{15}$ duplex is also likely to be as homogenous. Importantly, thermodynamic parameters cannot be extracted from these thermal melting profiles at acidic pH, as they could be complicated by depurination that prevents reversibility of the melts. For this reason, in this case, thermal denaturation cannot be used to establish a two-state transition. Thus, this is not a 'melting' experiment characteristic of a two-state transition, but the characterization of the thermal response of such $dA_{15}$ duplexes. However, in order to establish whether this duplex denaturation is two state, we carried out a pH denaturation of the $dA_{15}$ duplexes (see pH-induced structural transition probed by CD section).

The sharpness of the thermal melting transitions observed for the $dA_{15}$ duplexes is indicative of negligible slipped intermediates (45,46). Furthermore, literature studies on the poly rA duplexes of varying lengths have shown that slipped structures and intermediates occur only when the A-tracts approach lengths greater than $rA_{30}$ (45). However, in order to confirm that this is indeed the case, we performed fluorescence quenching experiments to measure the distance between two 3' termini in the $dA_{15}$ duplex, by a previously described method (31,33). Samples were prepared by mixing 1:50 3'-TMR-$dA_{15}$:3'-Dabcyl-$dA_{15}$ (100 nm:5 μM), 30 mM phosphate buffer, pH 3 such that every TMR-labeled $dA_{15}$ strand is incorporated into a duplex containing Dabcyl-labeled $dA_{15}$ strand. Any change in TMR fluorescence intensity will be due to quenching by Dabcyl-$dA_{15}$ strand present in the duplex. The quenching efficiency in these dually labeled complexes was found to be 50% as compared to similarly prepared 1:50 3'-TMR-$dA_{15}$:unlabeled $dA_{15}$ (100 nm:5 μM) complexes (see FIG. 5A). Readings were normalized to the fluorescence value of each of the samples, when they were taken to pH 7. This accounts for fluorescence changes due to both environmental effects of structure formation as well as pH effects. This quenching efficiency translates to an interfluorophore distance of 26±5 Å, incorporating the distance resolution due to fluorophore linker lengths (31, 33, 47). Given that the diameter of the pi-helix is ~22 Å, this translates to a maximum slippage of not more than one base in the $dA_{15}$ duplex. This is consistent with the melting studies that show at these segment lengths, the $dA_{15}$ duplex does not undergo any significant slipped structure formation. An equivalent of one-base slippage is seen even in the 5'E and 3'E intercalation topologies in i-motifs.

pH-induced structural transition probed by CD. The existence of two differently structured forms of $dA_{15}$ as a function of pH prompted us to investigate the potential of $dA_{15}$ as a nanoscale transducer, converting a proton input, into a conformational change of the poly dA single helix. For this it was essential to determine whether $dA_{15}$ showed a pH induced structural transition in solution as well. Five micromolar $dA_{15}$ was incubated in buffers of different pH ranging from pH 3 to 7 with a ~0.2 pH unit increment and the CD value at 217 nm was plotted as a function of pH (inset: FIG. 1B). A well-defined sharp transition centered at pH 4.8 was observed, indicating that the transition was two-state.

Reversible pH-induced structural transition in poly dA. Next we investigated whether poly $dA_{15}$ was capable of undergoing a reversible pH induced conformational switch from structured single helix to parallel duplex at pH 3.0. To an unbuffered solution of 5 μM $dA_{15}$ at pH 7, we added acid (HCl) and base (NaOH) alternately to accordingly switch the pH of the solution from 7 to 3 reversibly. Molecular switching was visualized by monitoring CD at 262 nm where signals were very different for the single and double helical forms. As evident from FIG. 6A, $dA_{15}$ can switch efficiently and reversibly between the two different states with change in pH without any significant loss in efficiency. This demonstrated that poly $dA_{15}$ was able to respond to a proton input, by changing its structure as evident from the changes in its CD properties.

Figure 6:
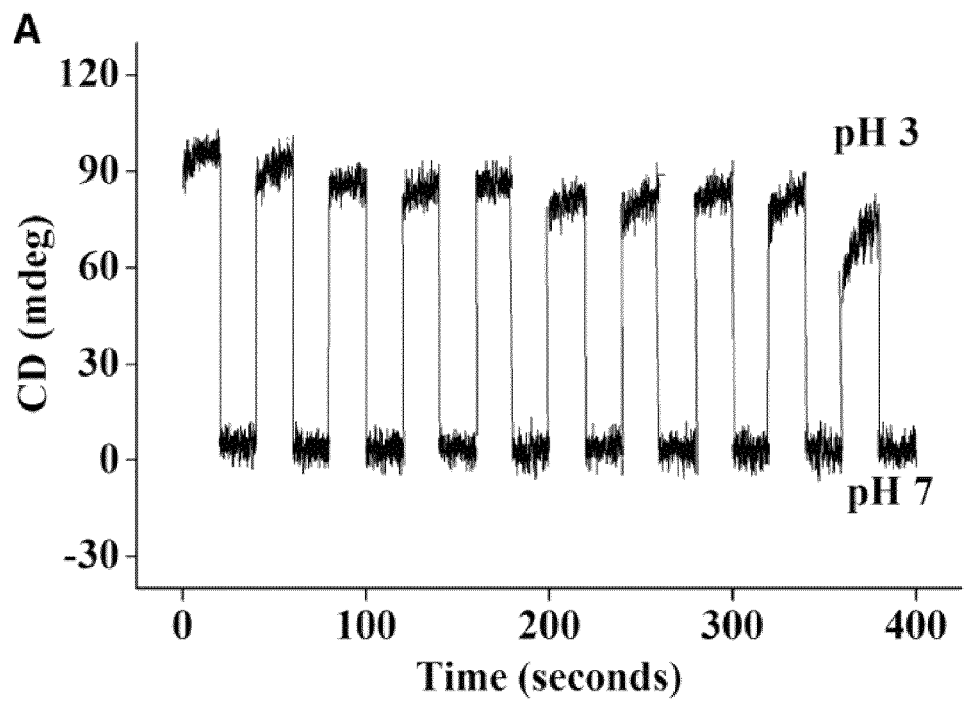
FIG. 6A is a graph of an illustrative CD of $dA_{15}$ at 262 nm demonstrating switching between single helix and duplex upon alternately cycling between pH 7 and pH 3 ($Na^+$ concentration at the end of 10th cycle~1.5 mM).
FIG. 6B is a graph illustrating the kinetics of transition of $dA_{15}$ from single helical to double helical form (shown in magenta) and vice versa (shown in black) probed by fluorescence from TAMRA.
Figure 6:
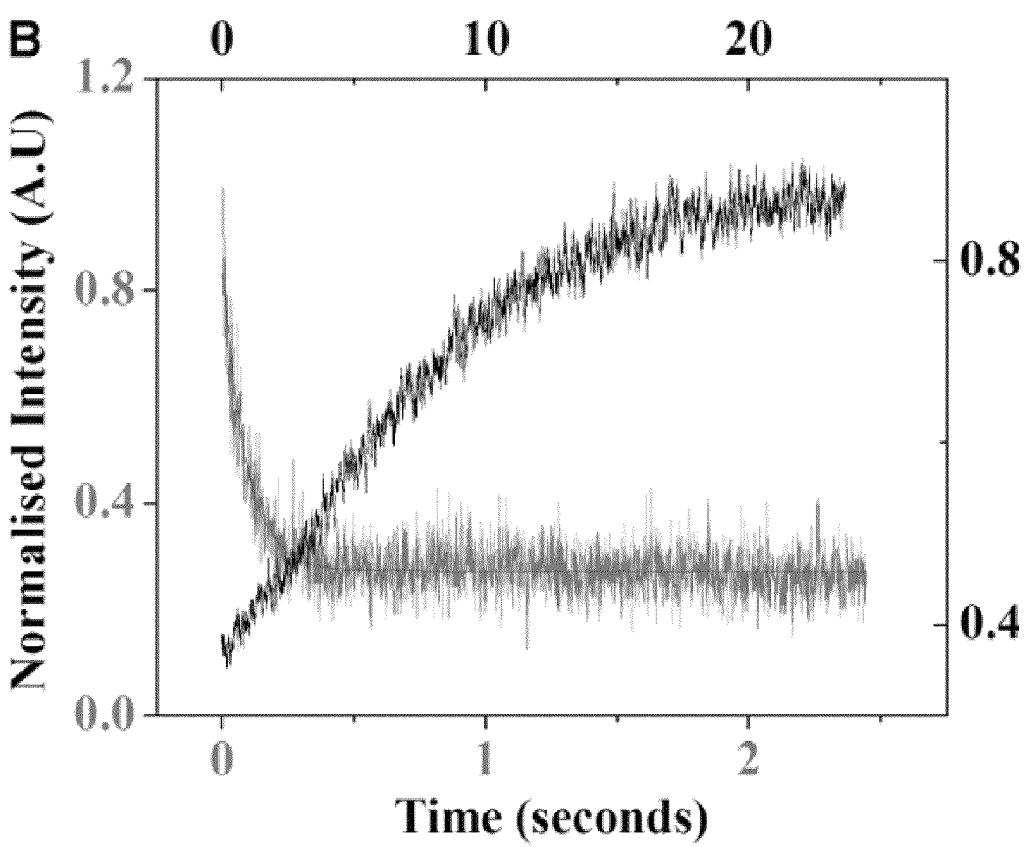
Figure 9:
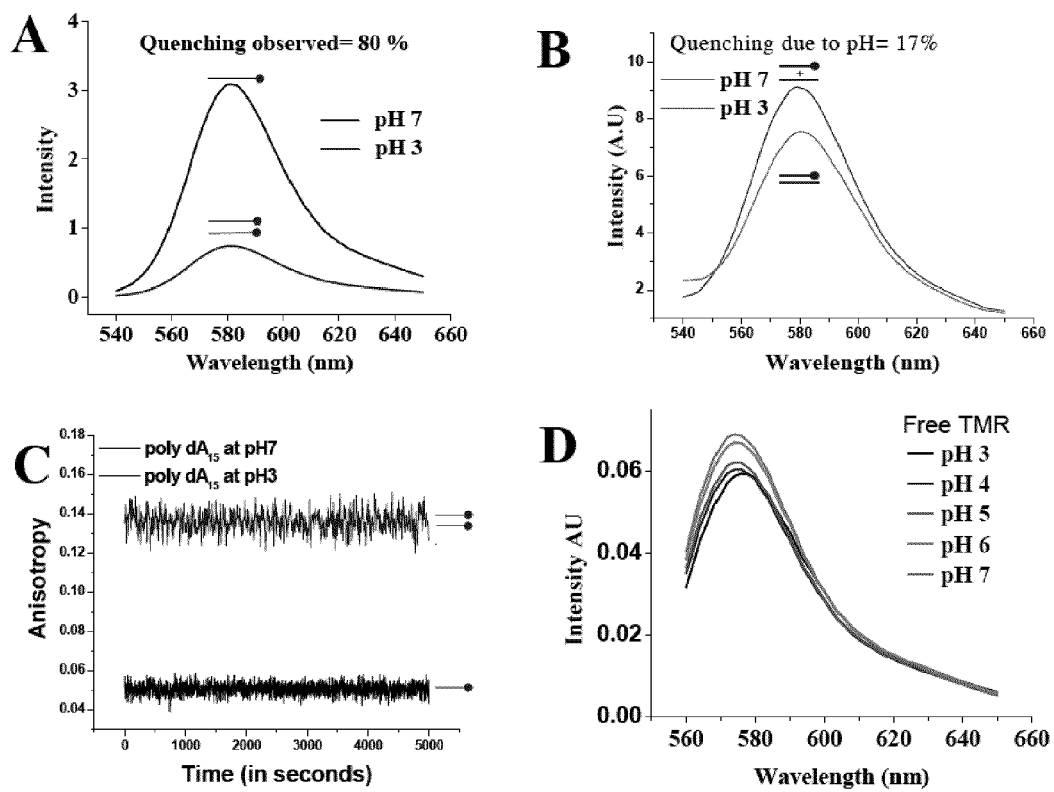
FIG. 9A is a graph illustrating fluorescence self-quenching of 5'-TAMRA-$dA_{15}$ in the duplex (pH 3) and single helical (pH 7) states.
FIG. 9B is a graph illustrating a control fluorescence experiment on 50:1 $dA_{15}$:5'-TAMRA-$dA_{15}$ at pH 3 and pH 7 showing quenching due to change in pH.
FIG. 9C is a graph showing anisotropy time series of duplexed and single helical $dA_{15}$.
FIG. 9D is a graph illustrating a control fluorescence experiment showing quenching due to pH decrease of free TMR.
Figure 20:
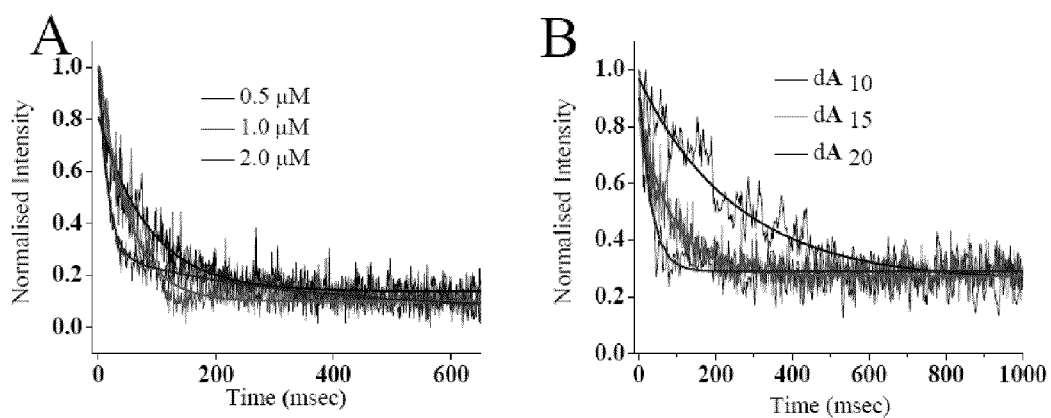
FIG. 20A is an illustrative graph of the concentration dependence of $dA_{15}$ duplex formation.
FIG. 20B is an illustrative graph of the kinetics of formation of poly dA duplex of different lengths at 0.5 μM concentration.

Dimerization may also be followed by fluorescence self quenching. In a parallel-stranded Π-helical configuration we would expect like termini in [5'-TAMRA-$dA_{15}$]$_2$ to have an interfluorophore distance of ~22 Å. Given that TAMRA has been shown to self-quench with a $R_o$ of 44 Å due to exciton coupling, that has been used to determine strand polarities in unusual nucleic acid motifs at low pH (47,48), we wanted to see if this change in fluorescence property could report on $dA_{15}$ duplexation. 5'-TAMRA labeled $dA_{15}$ was allowed to dimerize at pH 3 and the extent of quenching, relative to 5'-TAMRA-$dA_{15}$ at pH 7.0, determined. We found that the self quenching efficiency is greater than 80% consistent with the predicted strand polarity, and revealing that self-quenching could be used to follow dimerization (FIG. 9A and supporting text below for details). In order to measure the response times of $dA_{15}$ to this pH stimulus, kinetics experiments were performed using the fluorescence of 5'-TAMRA-$dA_{15}$ which self-quenches due to duplex formation. To 20 μl solution of 0.5 μM 5'-TAMRA-$dA_{15}$ in 100 μM phosphate buffer at pH 7, 5 μl of 50 mM pH 3 phosphate buffer was added to cause a pH jump to 3. Fluorescence of TAMRA-$dA_{15}$ quenches due to duplex formation as shown in FIG. 6B. The time scales of duplex formation at this concentration was found to be τ=90 ms demonstrating very fast duplexation. Association time scale was found to depend on concentration of the poly $dA_{15}$ strand used (see FIG. 20 and associated discussion), emphasizing the intermolecular nature of the duplex formation. Similarly dissociation of duplex to single helix was also followed in a similar way where addition of 1 M phosphate buffer, from pH 7 to 0.5 μM $dA_{15}$ in 5 mM phosphate buffer to cause a pH jump to 7. This relieved the fluorescence of TAMRA from quenching which is manifested by increase in fluorescence (FIG. 6A). The time scale of duplex dissociation was found to be slower (~7 s) compared to its association. This is consistent with the compactness of the duplex as revealed by MD and high stability because of its electrically neutral character and high number of H-bonds per base pair.

Figure 7:
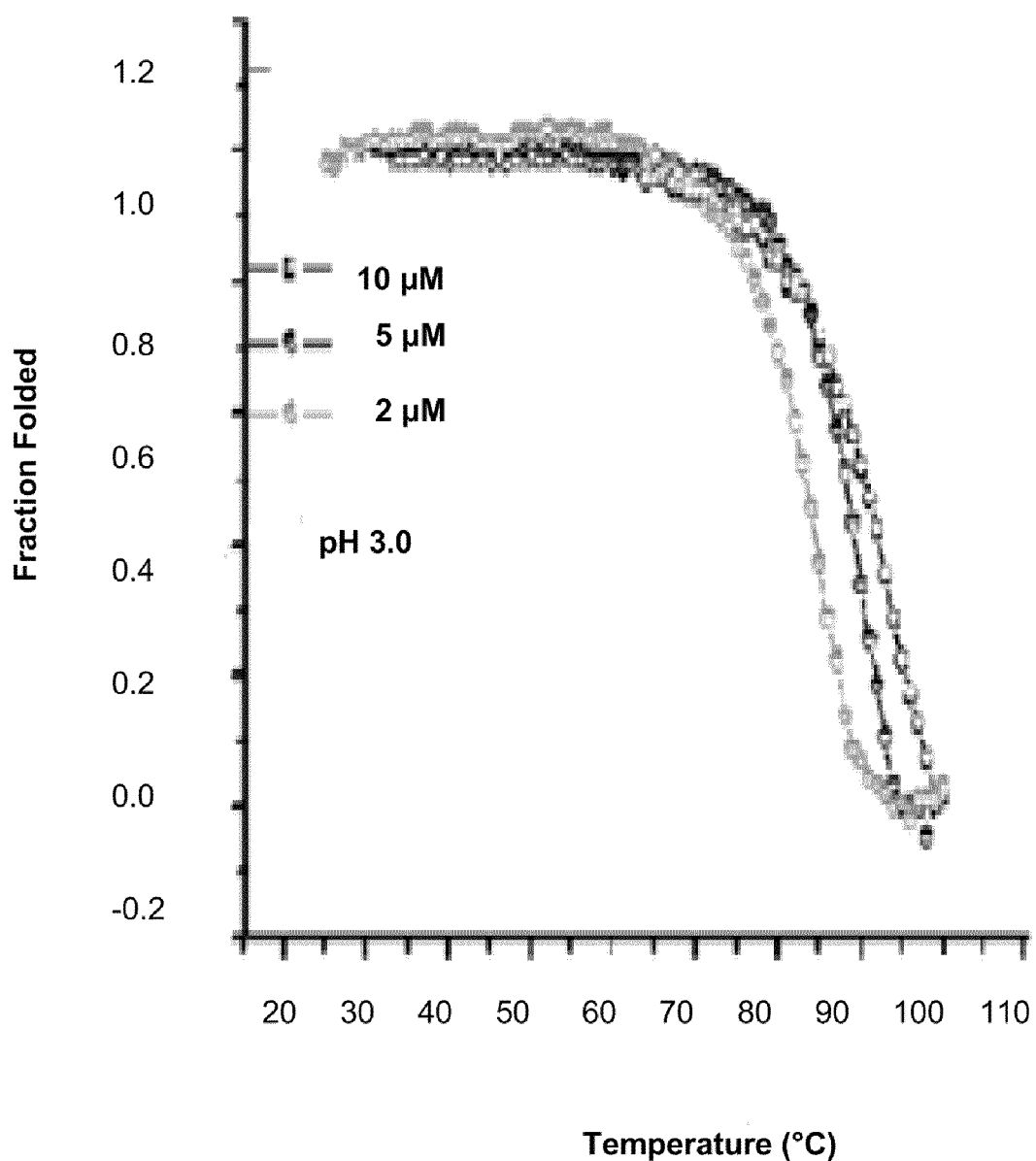
FIG. 7A is a graph of CD thermal melts of the poly dA duplex in 10 mM sodium phosphate buffer, pH 3.
FIGS. 7B and 7C are graphs of the melting of poly dA at pH 7 probed by UV and CD, respectively.
Figure 7:
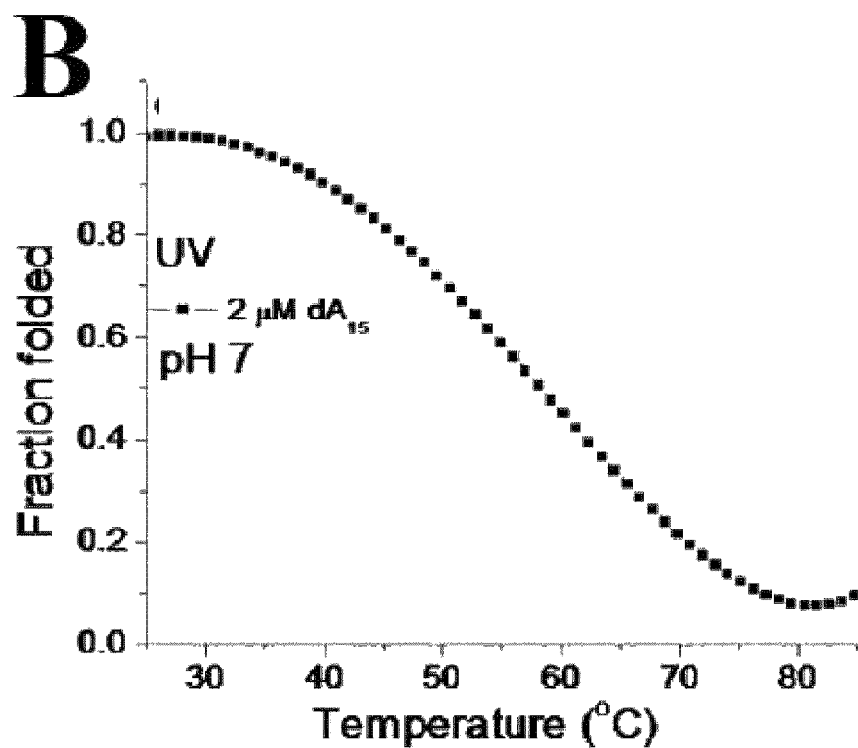
Figure 7:
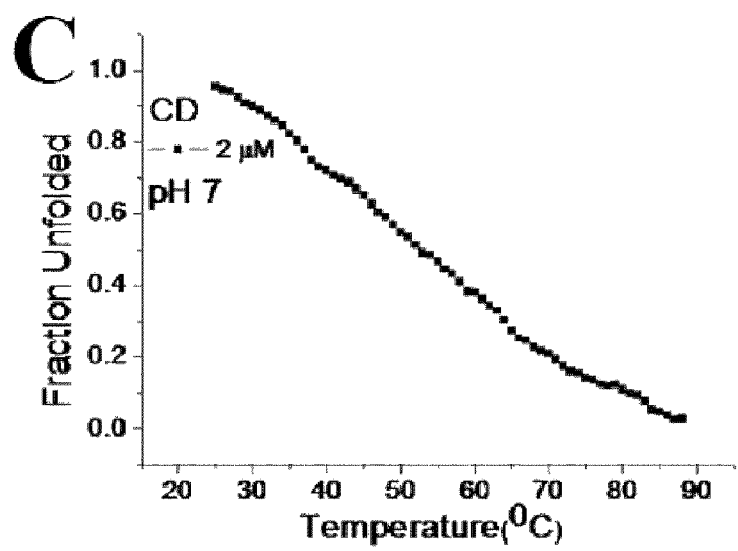

CD and UV melting Studies. To investigate the nature of the stabilizing interactions in $dA_{15}$, $dA_{15}$ samples at both acidic and neutral pH were thermally denatured and followed as a function of temperature both by circular dichroism (CD) and UV (FIG. 7). For acidic pH, samples were made as described in the main text at several concentrations ranging from 1 μM to 10 μM in 5 mM phosphate buffer, pH 3.0. For neutral pH, samples were made at 2 μM strand concentration in 5 mM phosphate buffer, pH 7. All the samples were investigated in the temperature regime of 20° C. to 100° C. following the absorbance at 260 nm by UV spectrometry or circular dichroism at 262 nm.

At neutral pH, $dA_{15}$ evidences a weakly structured form as seen from the broad and noncooperative melt in both UV and CD melting profiles (FIGS. 7B and 7C). However, the melting temperatures were different as obtained from UV ($T_{1/2}$=46° C.) and CD ($T_{1/2}$=53° C.). This is due to the fact that two different properties of the complex are followed by UV (base stacking) and CD (chirality). As shown in the main text (FIG. 2B) the 280 nm band in CD observed at pH 7.0 arises from a forbidden (n–π*) transition which is observable when water is excluded from the bases, as happens in a stacked conformation (49). This indicates that $dA_{15}$ is structured at neutral pH, stabilized majorly by stacking interactions. The loss of this band on heating implies the loss of stacking interactions. This is in line with previous findings (50) on single helices of poly dA that suggest that stacking interactions are the main driving forces in the poly dA single helix. At pH 3.0, however, $dA_{15}$ shows a much better defined sigmoidal thermal transition both in UV and CD indicating a structure that is cooperatively held (FIG. 5B, FIG. 7A). There is a strong dependence of $T_{1/2}$ on strand concentration as can be seen from the melting profiles consistent with the duplex being an intermolecular complex. Extracting thermodynamic parameters from these melting profiles is not possible as it is well documented that at acidic pH, adenosine homopolymers undergo depurination at elevated temperatures. Thus, these thermally induced transitions cannot be considered reversible.

TABLE 2

Concentration dependence of the duplex thermal stability as probed by CD.

| Concentration (μM) | $T_{1/2}$ (in °C.) |
|---|---|
| 2 | 83 |
| 5 | 88 |
| 10 | 90 |

Fluorescence experiments. Fluorescence spectra of TAMRA-TAMRA self quenching was recorded on a JASCO J-815 Spectropolarimeter equipped with a fluorescence detector and in 10 mm path length quartz cuvette. Prior to acquisition samples were diluted 5 fold in the cuvette. Samples were excited at 520 nm and emission was recorded between 540-700 nm, at scan rate of 1 nm/sec. The working formula used for the calculation of the distances is the following Equation I:

$$E = 1 - f_{D/A}/f_D = R_o^6/(R^6 + R_o^6)$$

Where $f_{D/A}$=fluorescence intensity in the presence of both the donor and acceptor; $f_D$=fluorescence intensity of the donor only; E=efficiency of energy transfer; $R_o$=Förster distance; and R=distance between the donor and acceptor. The distances between the labeled strands were calculated using fluorescence intensity of the complex at pH 3.0 ($f_{D/A}$) and the fluorescence intensity of samples at pH 7 ($f_D$). The Förster distance ($R_o$) for TAMRA-TAMRA self-quenching was 44 Å as described previously (52). Estimates of the relevant distances were obtained from the MD simulated model of the poly dA duplex incorporating the linkers.

As a control for alteration in TAMRA fluorescence due to environmental effects such as pH change and structural effects samples were prepared at total strand concentration 5 μM with 50:1 $dA_{15}$:5'-TAMRA-$dA_{15}$ such that every TAMRA-$dA_{15}$ strand is statistically incorporated into a duplex with only one TAMRA label. When the pH of this sample is changed from 7 to 3.0 we observed ~17% decrease in fluorescence which is used as a correction factor for doubly-labeled TAMRA duplexes which yields the contribution purely due to self-quenching (see FIG. 9B). In order to confirm that this quenching occurs because of proximal position of the fluorophores in the duplex and not by the dimer formation between the fluorophores we measured the anisotropy of the fluorophores at pH, 3 and 7. Anisotropy trajectories of the fluorophores at different pH, shown in the FIG. 9C, indicates that the fluorophores are rotating freely confirming that self-quenching is solely due to proximal position of fluorophores due to parallel duplex formation.

To calculate the distance between the two like ends of the duplex TMR-DABCYL fluorophore-quencher pair was used with $R_o$ of 26 Å (52). Dually labeled duplex was made with a 1:50 TMR-$dA_{15}$: DABCYL-$dA_{15}$. This ensured that every 3'-TMR-$dA_{15}$ was paired with a Dabcyl $dA_{15}$. Homo-Dabcyl-duplexes, which are the major species, are fluorescently silent and do not affect the experiment. 1:50 3'-TMR-$dA_{15}$:$dA_{15}$ served as a control for donor-only labeled duplex ($f_D$). The fluorescence intensity of the control ($f_D$) at pH 3 was normalized to the value of intensity upon giving the sample a pH jump to pH 7, thus correcting for any concentration effects. Thus the fluorescence intensity in the presence of the quencher in the doubly labeled duplex ($f_{DA}$) at pH 3 was measured and normalized as described. The efficiency of energy transfer and hence the distance is calculated from the equation (1).

Figure 3:
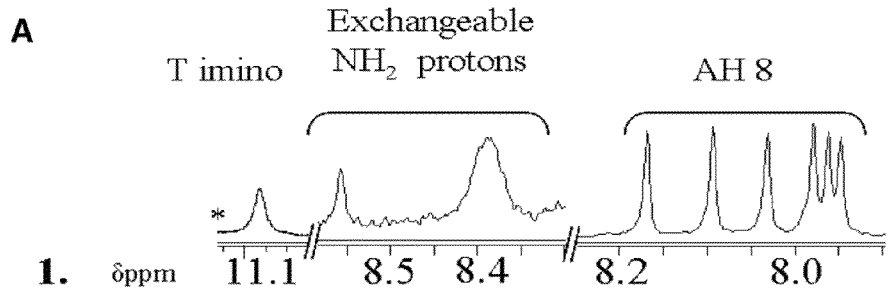
FIG. 3A is a series of illustrative 1D NMR spectra of 1 mM $dTA_6$ at 5° C. establishing $NH_2$ involved in H bonding at pH 3: (1) Spectra taken in 50 mM Na-acetate-d3 buffer pH 4.0 in 10% $D_2O$; (2) Spectra taken in Na-acetate-d3 buffer pH 4.0 in $D_2O$; (3) Spectra taken in pH 8 water ($Na^+$=50 mM).
FIG. 3B is a partial NOESY spectrum showing sugar H1'-Adenine H8 contacts of $dTA_6$ at pH 4 Na-acetate-d3 buffer. The NOE cross peaks a-l are assigned as follows. (a) A2(H8)-T1(CH$_3$); (b) A2(H8)-A2(H1'); (c) A3(H8)-A2(H1'); (d) A3(H8)-A3(H1'); (e) A4(H8)-A3(H1'); (f) A4(H8)-A4(H1'); (g) A5(H8)-A4(H1'); (h) A5(H8)-A5(H1'); (i) A6(H8)-A5(H1'); (j) A6(H8)-A6(H1'); (k) A7(H8)-A6(H1'); (l) A7(H8)-A7(H1').
Figure 3:
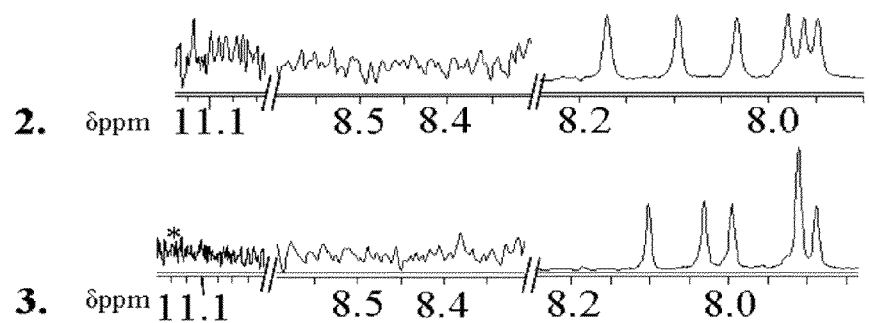
Figure 3:
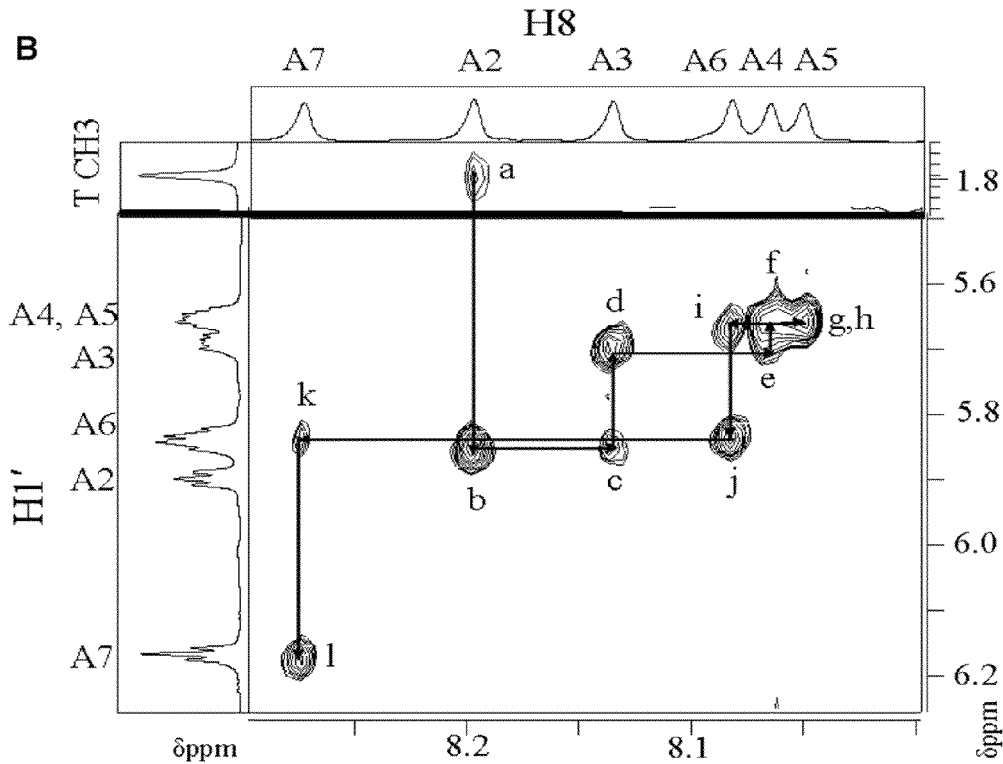
Figure 10:
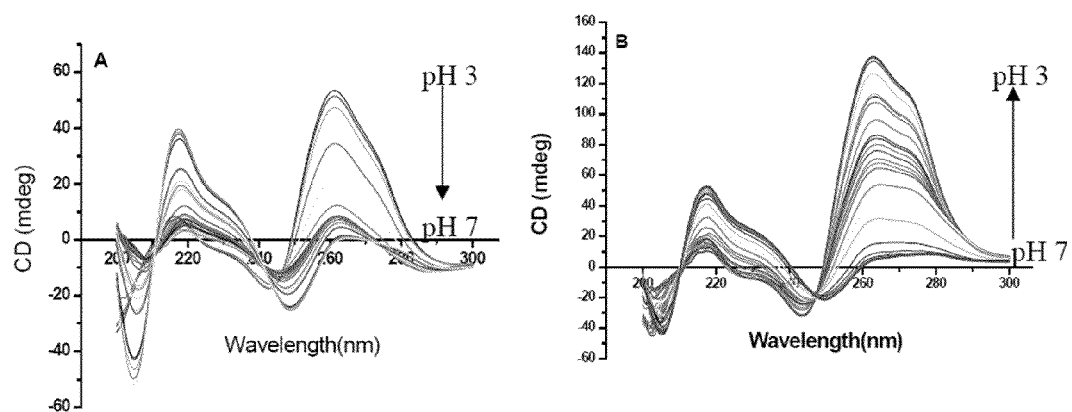
FIG. 10A is a graph illustrating the structural transition of $dA_{15}$ from pH 3 to pH 7.
FIG. 10B is a graph illustrating the structural transition from pH 7 to pH 3. Transitions are brought about by adding 5 µL of 0.01 N HCl or NaOH.

Effect of pH on free TMR (tetramethylrhodamine-5-maleimide) was also checked as shown in FIG. 3D. The fluorescence emission spectra of 500 nM free TMR in 1 mM NaCl, pH 7 recorded using 550 nm excitation and emission between 560 nm-650 nm. The pH was altered incrementally by adding requisite amount of 0.5 mM phosphate buffer of desired pH and spectra recorded. The spectrum at any given pH was normalized to its value at pH 7 which eliminated differences due to experimental variations in concentration. At pH 3, 4 and 5 14%, 13% and 10% quenching at 575 nm was observed compared to pH 7, respectively.

pH titration. In order to follow the pH induced structural transition in poly dA kinetically, we formed two samples of poly dA of 5 μM at pH 3 and pH 7 in unbuffered solutions. We increased the pH of pH 3 solutions by 0.2 pH units incrementally till pH 7. Similarly we decreased the pH of the solution at pH 7 by 0.2 pH units until it reaches pH 7. Structural transition in these two titrations was visualized by circular dichroism at 262 nm. CD profiles at different pH are shown in FIG. 10. This indicates the reproducibility in conformational switching in this system.

Figure 11:
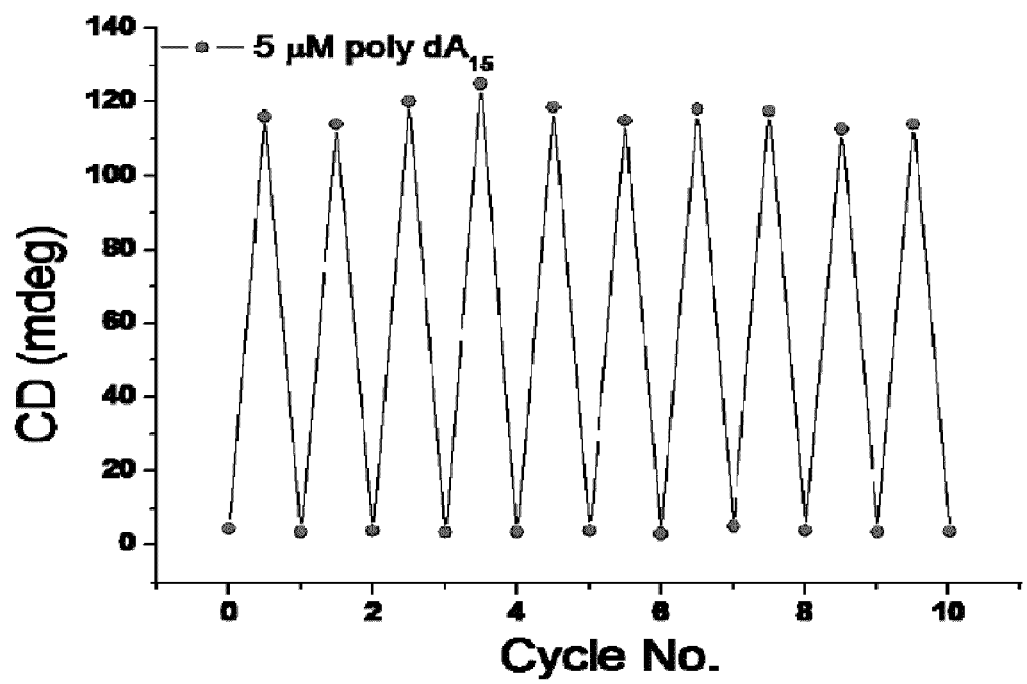
FIG. 11 is a graph illustrating the conformational switching of poly $dA_{15}$ between single and double helical forms visualized by CD at 262 nm, by alternate addition of acid and base respectively.

Switching and cycling. As mentioned above, cycling between single stranded helix to double stranded form by the poly dA was probed by circular dichroism at suitable wavelength. Samples of 5 μM $dA_{15}$ were prepared in unbuffered solution at pH 7 and pH of the solution was changed to pH 3 and vice versa by alternate addition of 0.01N acid and base. Double helix formation was probed by CD at 262 nm where the duplex shows high positive CD and the single helix shows negligible CD. As shown in FIG. 11, over ten cycles we observed efficient cycling by poly dA.

Figure 2:
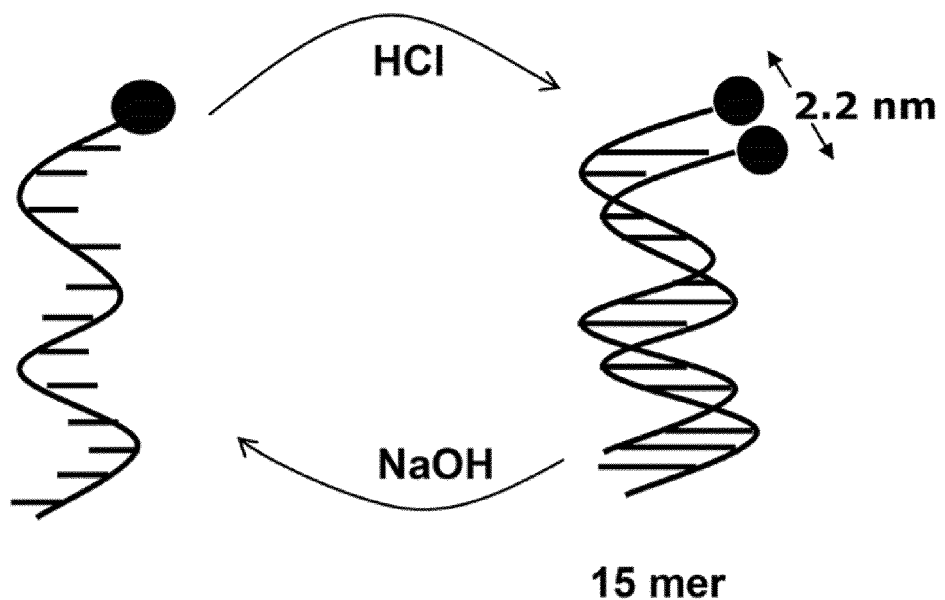
FIG. 2A is an illustrative schematic showing poly $dA_{15}$ changing between single helix to duplex conformations induced by alternate addition of acid and base respectively.
FIG. 2B shows the base pairing scheme in $AH^+$—$H^+A$ base pairs comprising protonated adenosines.
Figure 2:
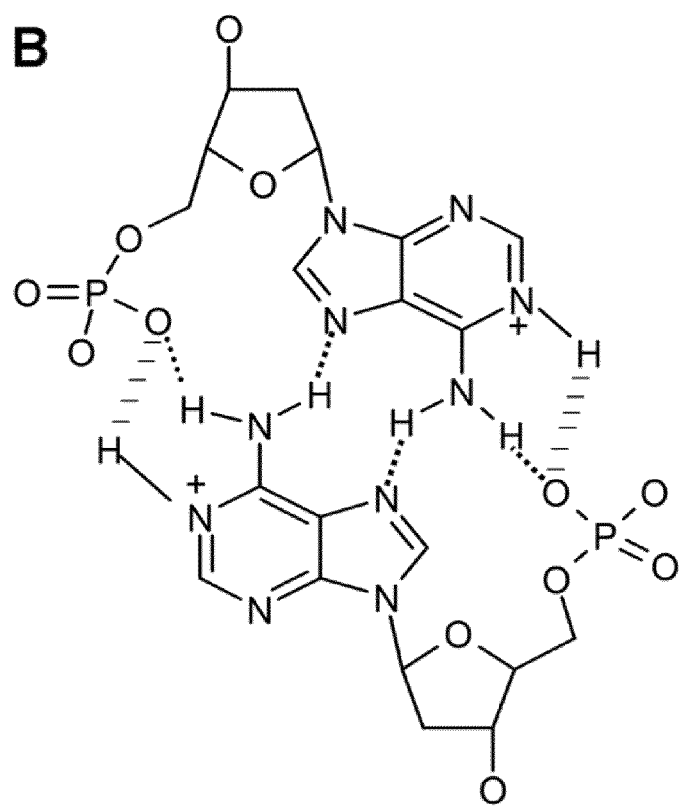
Figure 12:
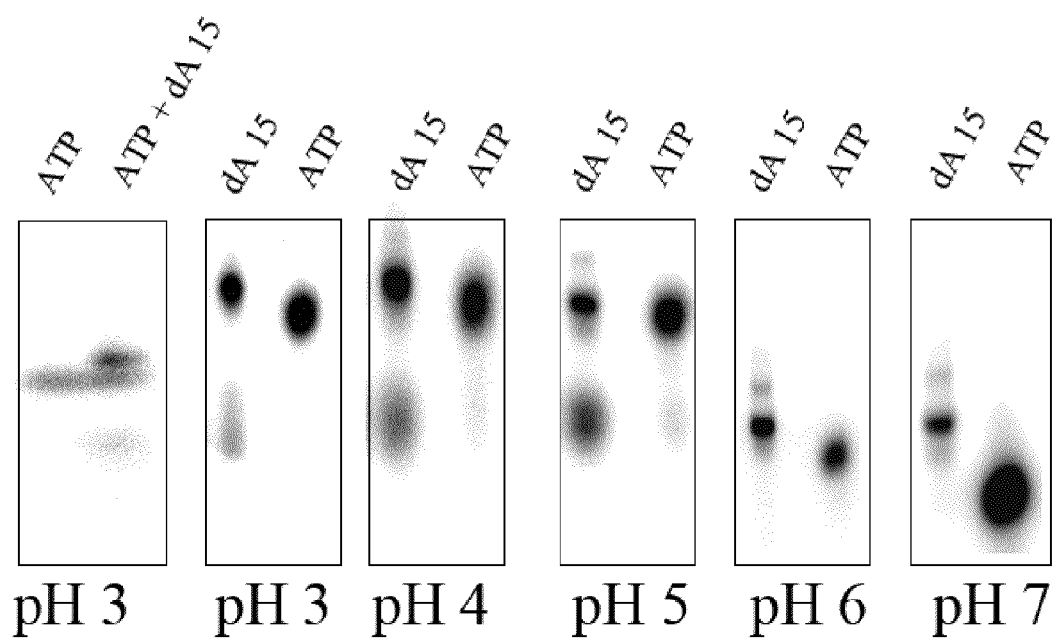
FIG. 12 is a series of illustrative gel images of $^{32}$P-labeled poly $dA_{15}$ ($dA_{15}$*) in comparison with $^{32}$P-ATP (ATP*) to show that the bands of interest are not due to the latter. From left: Gel showing Lane 1: ATP* alone; Lane 2: an externally added amount of ATP* to $dA_{15}$* at pH 3. Gels showing Lane 1: $dA_{15}$*, Lane 2: ATP* at the pH indicated below. Electrophoresis was performed in 15% native PAGE in 1× Robinson-Britton buffer of required pH at 20° C. at 10 V/cm and visualized using PhosphorImager. Note that migration of ATP* changes from pH 6 to pH 5 due to protonation on N1 of adenine.

Gel Electrophoresis. FIG. 2A showed that $dA_{15}$ adopted two forms having different electrophoretic mobilities as a function of pH. In order to ensure that the observed bands are not due to residual $P^{32}$-ATP used for labeling $dA_{15}$, $P^{32}$-ATP was mixed with radiolabelled $dA_{15}$ at the relevant pH and loaded in the gel (see leftmost panel, FIG. 12). This was also done at various indicated pH values (see remaining panels) and it was noted that both bands observed were due to labeled $dA_{15}$ and not $P^{32}$-ATP.

Figure 13:
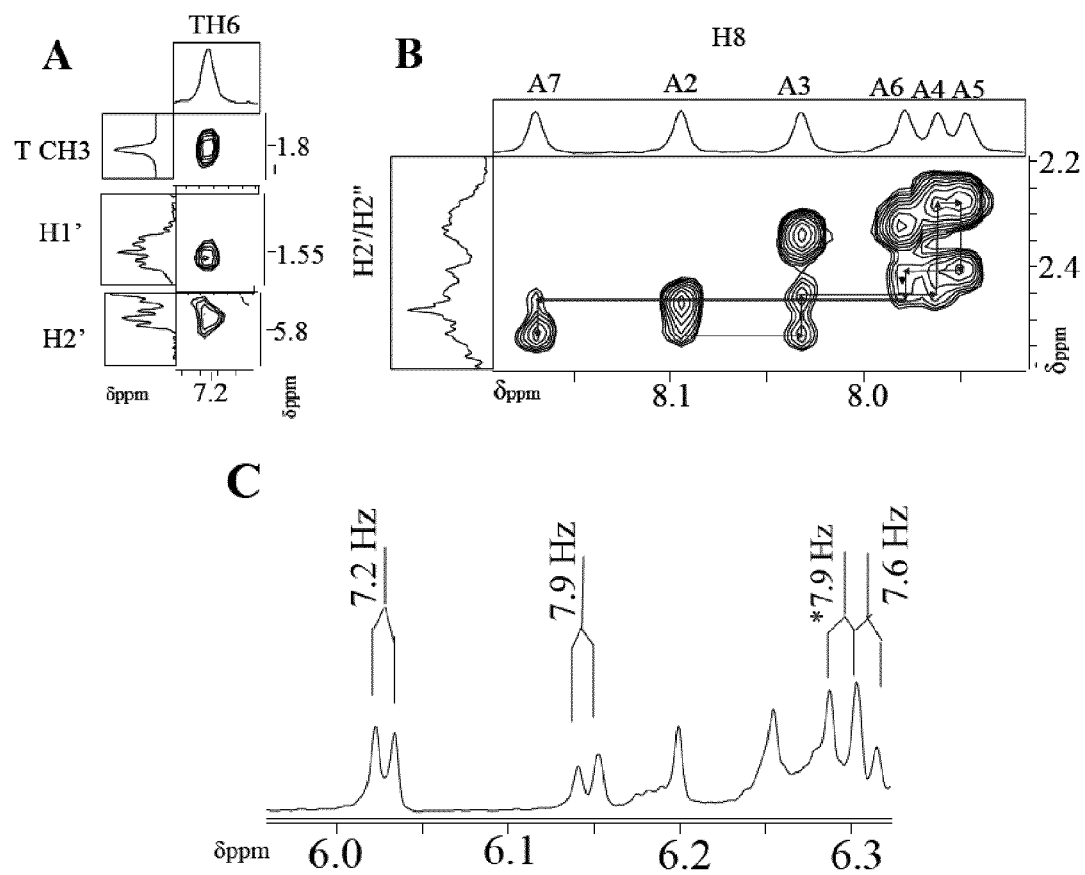
FIG. 13A is a partial NOESY spectrum in a 500 MHz Bruker NMR spectrometer showing NOE crosspeaks of thymine H6 with sugar protons establishing presence of a single thymine, characteristic of a unique conformational population.
FIG. 13B is a partial NOESY spectrum of the NOE walk corresponding to H2'/H2"-Adenine H8 contacts in 1 mM $dTA_6$, pH 4, 50 mM d3-Na-acetate.
FIG. 13C is an illustrative 1D spectrum of $dTA_6$, pH 4, d3-Na-acetate showing splitting of several adenine H2 protons characteristic of N1 protonation at these positions. Also shown are the corresponding $^3$J-values; '*' indicates that this value was obtained from the $D_2O$ exchanged spectrum (data not shown) which showed these peak separations with greater clarity.
Figure 14:
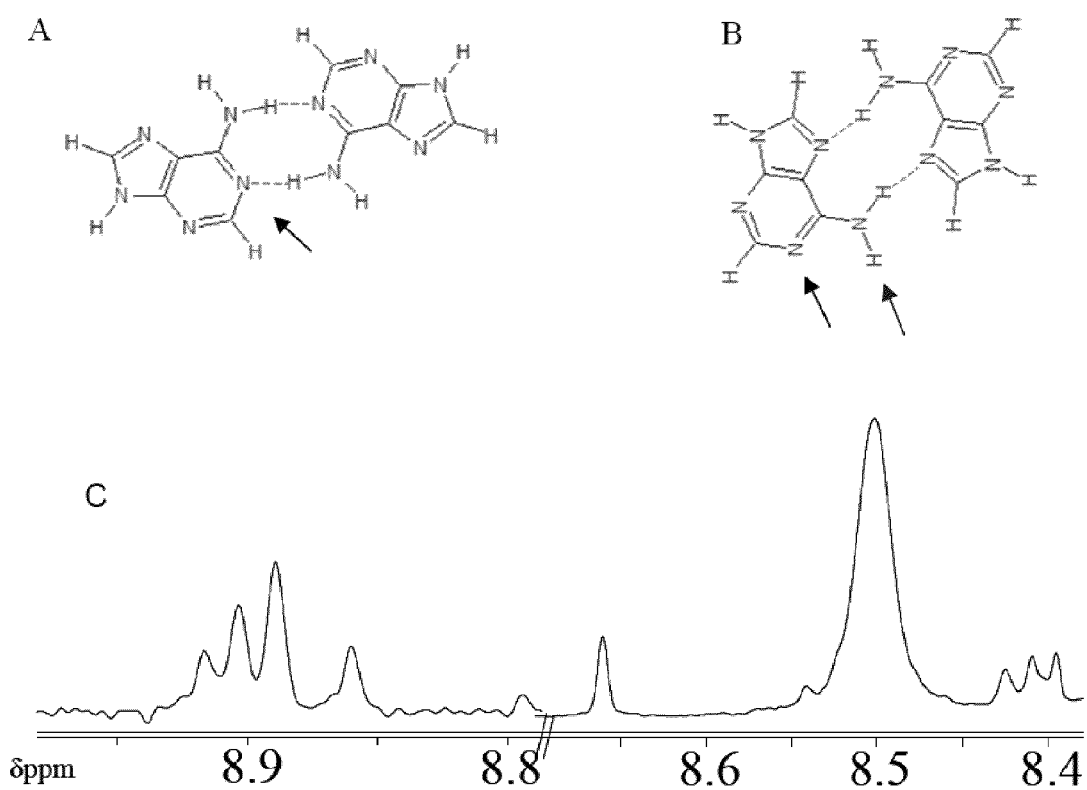
FIG. 14 is an illustration of schemes predicted for both types of A-A base pairs in parallel duplexes.

1D and 2D NMR. FIG. 13A shows NOE crosspeaks between thymine H6 and its corresponding sugar H1' and H2'/H2". The presence of a single crosspeak evidences the formation of a single conformational species in bulk at pH 4. FIG. 13B shows NOE crosspeaks and the associated NOE walk for the adenine H8 and sugar H2'/H2". The NOE connectivities between these protons are commensurate with a parallel stranded $dTA_6$ duplex. FIG. 13C shows the region of 1D spectrum corresponding to the adenine H2 protons. It was observed that several H2 protons were split with a constant $^3$J coupling of ~7.5 Hz indicating the presence of another proton in the same spin system. Importantly, these H2 protons showed no splitting at pH 8. It has been shown in other N1-protonated pyridiazine systems in water, that at acidic pH, protonation at N1 sites splits the H2 protons due $^3J_{H-H}$ coupling (53). This therefore clearly points to N1 protonation in the $dTA_6$ duplex at pH 4. Importantly N1 protonation rules out A-A base-pairing via the reverse Watson Crick faces of adenine and supports base-pairing via the reverse Hoogsteen faces (See FIG. 14). This is highly consistent with the MD simulated duplex structure.

Establishing Reverse-Hoogsteen base pairing scheme. In the literature only two kind of A-A homo base pairs have been reported in the context of A-containing sequences that form parallel DNA duplexes (54). These are shown below in FIG. 14. The reverse Watson-Crick mode of base pairing can readily be eliminated due to the fact that N1 in dTA6 is protonated. Protonation at the N1 site cannot support reverse WC base pairing as N1 has to be unprotonated in order to function as an H-bond acceptor for the N6 amino group (See FIG. 14A). This effectively means that the $AH^+$—$H^+A$ base pairing can only be of the reverse Hoogsteen type. Moreover, the nucleobase positioning of the reverse Hoogsteen faces is compliant with simultaneous N1 protonation on both bases with the $N1_+$ sites electrostatically interacting with the phosphate backbone of the opposite strand. Furthermore, in the 1D-spectrum at 800 MHz, we observe two kinds of $NH_{2b}$ resonances and this is consistent with the reverse Hoogsteen type base-pairing where the two $NH_2$ protons are H-bonded to two different chemical entities.

Figure 15:
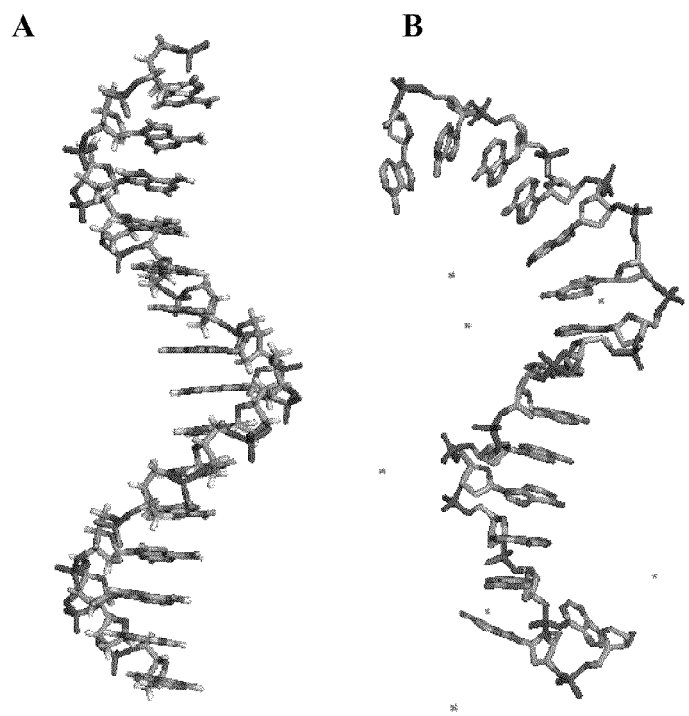
FIG. 15A is an illustration of a starting conformer of the single stranded poly dA constructed for MD simulation.
FIG. 15B illustrates a poly $dA_{15}$ single helix obtained after 20 ns simulation. The single helix is 9-fold with a helix pitch of ~26 Å and a rise per base ~2.9 Å. The adenine planes are tilted with respect to the helical axis. All the glycosidic angles of adenosines are anti with respect the sugar, as observed also in the poly rA single helix. Sugar puckers are found to be predominantly C2'-endo.
Figure 19:
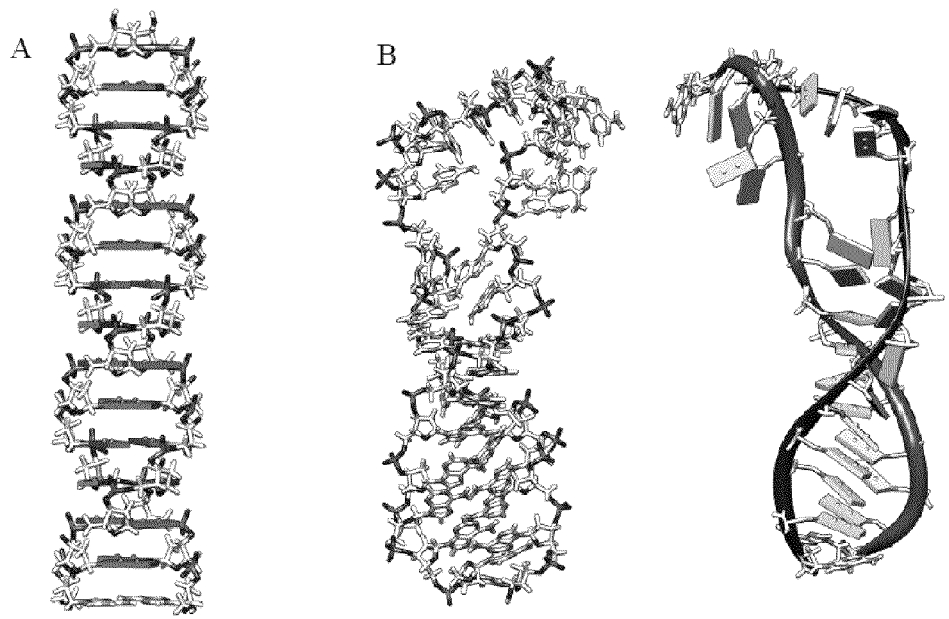
FIG. 19A is a model showing the starting structure for the MD simulation. Importantly, bases are not tilted with respect to the helix axis.
FIG. 19B illustrates two different representations of the structure of the unprotonated duplex after MD simulation. It shows a loose base pairing at the 3'-end.

Molecular Dynamics Study. Poly dA single helix: The poly dA single strand was built in NAMOT 2 software and MD simulations performed using AMBER9 (55) with the all-atom AMBER03 force field. FIG. 15 shows the structure of the helix before and after MD simulation. Poly dA double helix: The starting conformations for the simulations were generated in the following way. The parallel Hoogsteen $AH_+$—$H_+A$ base pair (Leontis/Westhof Classification Legend 8 and Saenger classification II) with trans glycosidic bond orientation was made as described for the poly rA double helix using NAMOT 2 (56) and then multimerized to create a double helix. The pitch (30.4 Å) and rise per base pair (3.8 Å) was maintained as described for the poly rA double helix (51). The adenine protonation was modeled by adding H1 hydrogen to the N1 atom. Each adenine in every base pair was protonated. Added hydrogen for the protonated base was assigned as AMBER type H5. The partial charges for the protonated adenosine were obtained using the following procedure. Adenosines were protonated at N1 position and dimethyl phosphate molecules were optimized at HF/6-31G(d) level of theory using Gaussian program package (57). The Electrostatic surface potential (ESP) of the two molecules were used for calculating the partial charges of nucleotides (protonated DA3, DA, DA5). Antechamber (58) module of AMBER suite of programs was used to extract the ESP charges and a two stage fitting was done using the Amber's restrained electrostatic potential (RESP) (55) where the inter-molecular charge restraints and equivalency of atoms are considered as in Cieplak et at (59). This structure was the starting point for the MD simulations of the protonated poly dA double helix (See FIG. 19A). An additional simulation was also run on a poly dA double helix without protonation of adenosines as a control (See FIG. 19).

MD simulation protocol: Using the LEaP module in AMBER, the DNA structure was immersed in a water box using the TIP3P model for water (60). The box dimensions ensured a 10 Å salvation shell around the DNA structure. In addition, some water molecules were replaced by $Na_+$ ions to neutralize the negative charge on the DNA phosphates in the case of the unprotonated double helix. The system was then subjected to the equilibration protocol as outlined previously (61-63). All MD simulations used the AMBER9 software package with the all-atom AMBER03 force field (63). The electrostatic interactions were calculated with the Particle Mesh Ewald (PME) method using a cubic B-spline interpolation of order 4 and a $10_{-4}$ tolerance set for the direct space sum cutoff (63-64). A real space cut off of 9 Å was used both for the electrostatic and van-der Waals interactions with a non-bond list update frequency of 10. It is important to note that in the constructed model of the poly dA duplex, the $AH_+$—$H_+A$ base pairs were perfectly planar with 0° tilt to the perpendicular to the helix long axis (See FIG. 19A). We used a distance restraint of 1.9 Å between the hydrogen of the base (N6-H1) and the oxygen attached to phosphate (O2P) for each base as seen in the $AH_+$—$_+HA$ base pairing in the fiber diffraction structure of poly rA.

MD simulation on single stranded poly dA. It is generally assumed that the helical structure of nucleic acids are formed from double stranded regions stabilized by base paring, following the classical Watson-crick base pairing model. In the absence of base pairing the random coil is usually considered as the alternative structure. However, at pH 7 both poly rA as well as poly dA show very high Circular Dichroism which is also distinct from the random coil signature. Further, they exhibit hyperchromicity in UV with increasing temperature.

Using NMR, small angle X-ray scattering and viscosity measurements it has been shown that poly rA actually exists as a structured single helix (65). In line with these observation, we see that poly $dA_{15}$ at pH 7 recapitulates the behavior of poly rA experimentally. Further, MDS on the poly dA single strand showed a nicely structured helical form driven by stacking of the large aromatic faces of adenines (see FIG. 15 for helical parameters) which is also reflected experimentally in its CD spectrum.

Figure 16:
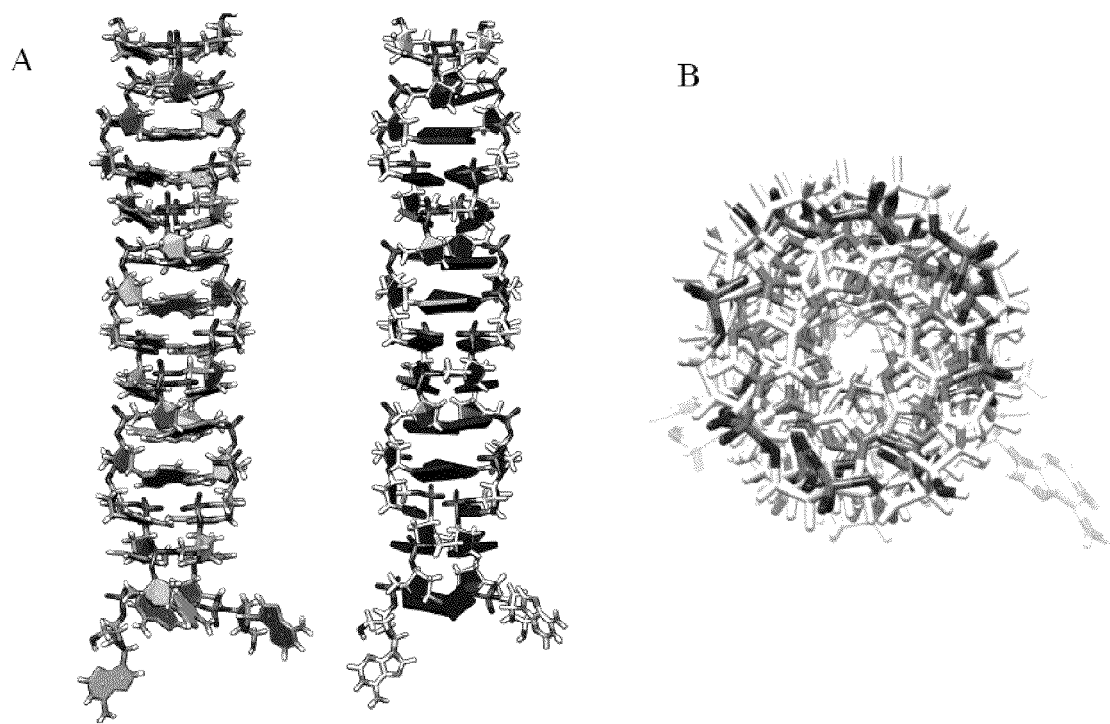
FIG. 16A illustrates two different representations of the structure of poly $dA_{15}$ parallel, protonated double helix after 20 ns molecular dynamics simulation incorporating a distance restraint.
FIG. 16B is an illustrative end on view of this structure showing the characteristic phosphate periphery surrounding the hydrophobic base stacked region in DNA duplexes.

MD Simulations on the protonated parallel, poly $dA_{15}$ duplex. The double helix was made using NAMOT 2 software and subjected to an MD simulation as described earlier. During the 20 ns simulation this duplex adopts and maintains a highly stable structure according to the model shown in FIG. 16. Interestingly, this duplex recapitulates perfectly the features of the poly rA double helix. This duplex is considerably stretched toward its long axis and composed of symmetrical $AH^+$—$H^+A$ base pairs. The helix is 8-fold; implying a ~45° turn angle per nucleotide and the pitch height is 31.2 Å. A dyad axis coincides with the helical axis which results in rotationally symmetric base pairs. Importantly, during the MD simulation, the perfectly planar $AH_+$—$H_+A$ base pairs in the model became tilted by ~12° with respect to horizontal to the helical axis—this is a characteristic feature of the base pairs in the poly rA duplex fiber diffracted structure. All the averaged helical parameters derived using CURVES 5.1 (66) are listed below:

| Chi | Gamma | Delta | Epsilon | Zeta | Alpha | Beta |
|---|---|---|---|---|---|---|
| −173.1 | 57.8 | 83.1 | −153 | −62.4 | −69.2 | −172.53 |
| Shift | Slide | Rise | Tilt | Roll | Twist | |
| 0.03 | −2.83 | 3.9 | −13 | −2.9 | 44.3 | |

Figure 17:
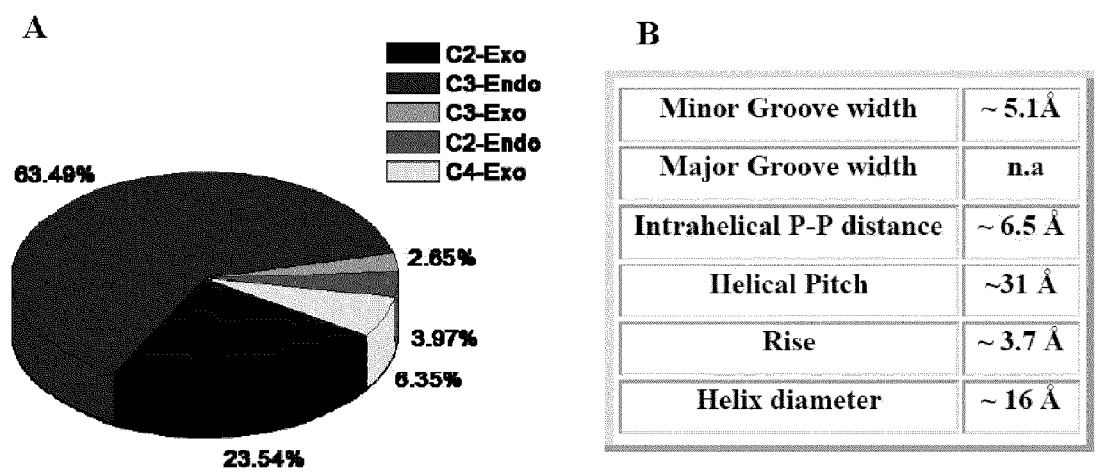
FIG. 17A is a pie chart showing frequency of different types of sugar puckers in the poly dA duplex.
FIG. 17B shows the major global helical parameters.

The parallel stranded poly $dA_{15}$ duplex adopts an overall right handed helical twist. Certain regions in the duplex show more helical twist (>50°) than other regions both locally as well as globally, while the mean twist is found to be ~45°. The axial rise for each step is in the range of 3.3 to 4.6 Å for the poly dA duplex similar to the poly rA helix (~3.9 Å). The glycosidic torsion angles are anti and the sugar puckers are mostly N type. Most of the sugars adopt c3'-endo conformations but c2'-exo, c4'-exo conformations are also found (see FIG. 17).

Figure 18:
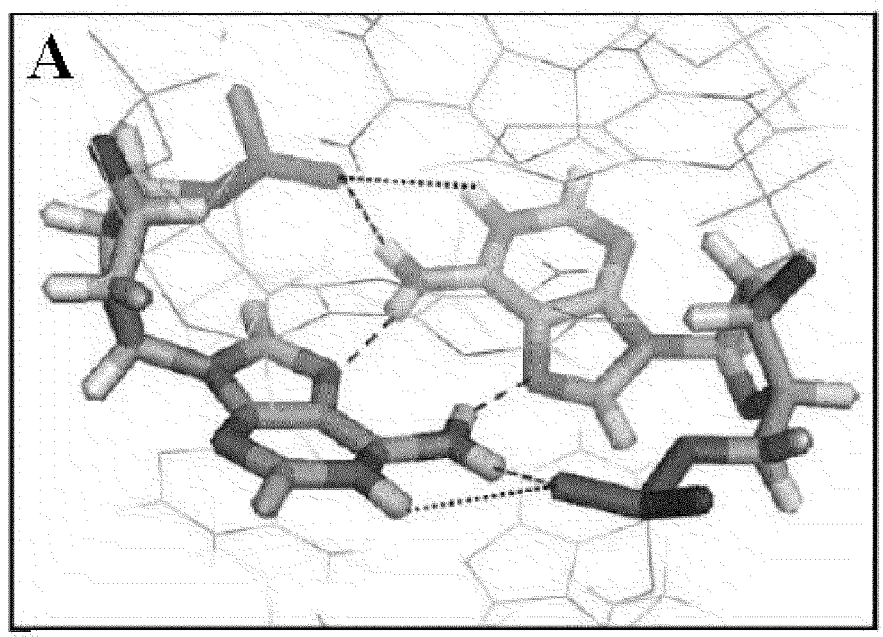
FIG. 18A illustrates the base pairing scheme of AH⁺—H⁺A.
FIG. 18B is an illustrative histogram showing the mean distance (in Å) between N1-H to O2P to be about 2.9 Å which is also ideal for H-bonding.
Figure 18:
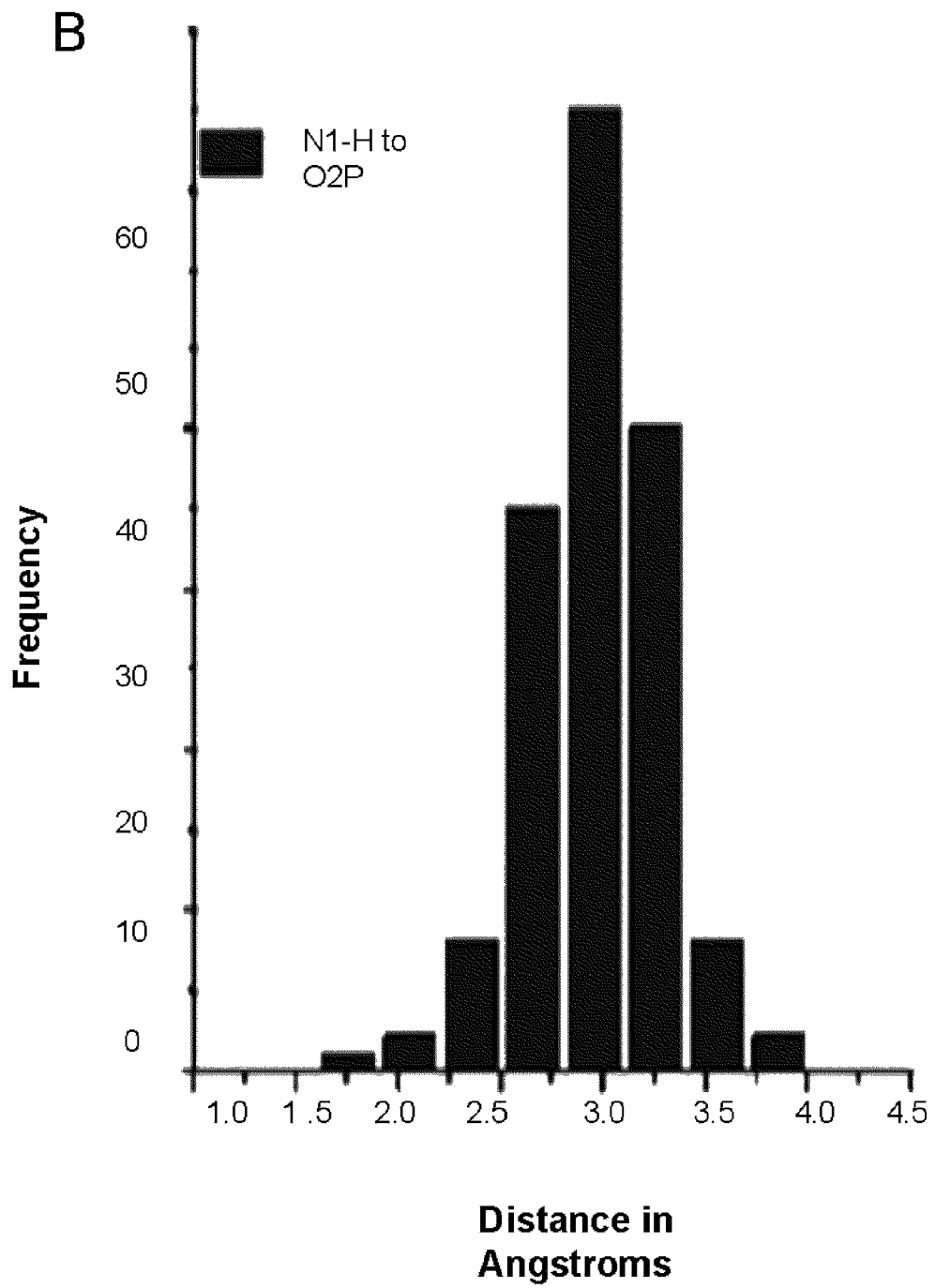

Base Pairing. Notably, the MD simulated structure reveals that N1-H moves to within the H-bonding distance from the O2P for all base pairs (final distance after MD: 2.9±0.3 Å, initial distance before MD: ~4 Å). A typical base pair is shown in FIG. 18A. This is not unusual considering that oxygen possesses two lone pairs capable of simultaneously forming two H-bonds. In the poly rA duplex, the N1-$H^+$ and $^-$O—P has been described as a salt bridge that serves to bring the phosphate close to the helix axis in order to facilitate H-bond formation between N6-H1 and O2P.

Even in poly dA, this inner salt effect is evident from the thermal stability studies (see salt dependence section in revised m/s) where the helix is destabilized with increasing ionic strength of the solution. However, the unusually high thermal stability of this duplex is in line with the extra strong proton-mediated interaction between N1-H$^+$ and $^-$O—P predicted by the MD simulation which would give rise to the equivalent of 6 H bonds per AH$^+$—H$^+$A base pair. This is also experimentally supported by the data on its dissociation kinetics. Structure formation due to protonation on N1 occurs on the millisecond time scale in line with the kinetics for protonation of any exposed site. However dissociation is substantially slower (in seconds) indicating reluctance for deprotonation at this site. This is in line with the proton at this site either being buried or held tightly by H-bonding. Thus, MD simulations combined with experimental data therefore suggests a possible additional role for the N1-H as an H-bond in addition to mediating an inner salt effect.

MD simulation on unprotonated duplex. It has been suggested (51) that the protonation of adenines causes electrostatic stabilization of the poly rA parallel duplex and that without protonation this duplex is unstable. Our experiments reveal a similar role for the N1 protonation in the poly dA duplex as well, strongly supported by MD simulations. As a control, we performed MD simulations on a parallel stranded poly dA duplex without N1 protonation. For this we constructed two kinds of parallel stranded poly dA duplexes with same pitch and rise as described for poly rA, where one had all C3'-endo sugar puckers and the other with all C2'-endo sugar puckers. In line with the proposed importance of N1 protonation, both these unprotonated duplexes were not stable (See FIG. 19). Although there is a dramatic departure from the initial structure, both strands did not collapse totally. There were regions at the 3'-end that were loosely associated, although the 5' end is totally frayed. This certainly reaffirmed the role of N1-protonation in stabilization of the parallel duplex. It is likely to (i) bring the phosphate on the opposite strand closer to the helical axis (ii) electrostatically stabilize the helix by making the whole entity electrically neutral and (iii) increase the number of H-bonds per the AH$^+$—H$^+$A base pair (see FIG. 18A). Thus we delineate a structure of the poly dA double helix and for the first time constructed an atomistic model of the poly dA based on MD simulations. These suggest an additional role for N1 protonation to what has been described thus far.

Concentration and Length dependence of kinetics of poly dA duplexation. In order to measure concentration dependence of the association dA$_{15}$, kinetics experiments were performed using the fluorescence of 3'-TMR-dA$_{15}$ which self-quenches due to duplex formation. To 20 µl of 0.50 µM, 1 µM and 2 µM 3'-TMR-dA$_{15}$ in 100 µM phosphate buffer at pH 7, 5 µL of 50 mM pH 3 phosphate buffer was added to cause a pH jump to pH 3. Fluorescence of TMR-dA$_{15}$ quenches due to duplex formation as shown in FIG. 9A. The FIG. 20A shows the self-quenching for TMR-dA$_{15}$ at strand concentrations of 0.5 µM, 1.0 µM and 2.0 µM respectively. Clearly, the association is diffusion-limited as well as dependent on concentration, emphasizing the intermolecular nature of the duplex formation. These curves fitted well to a second order rate equation (67) giving a second order rate constant of $k_{on}$=(5.3±0.5)×10$_7$ M$_{-1S-1}$ for all traces. This is further consistent with duplexation being bi-molecular. To see the effect of length of dA tract on association, similar experiments were performed with dA$_{10}$ and dA$_{20}$ at 0.5 µM strand concentrations (FIG. 20B). With increase in A-tract length, the reaction is faster (Table 3), indicative of larger K$_a$ for longer lengths of A-tracts in line with our expectations.

TABLE 3

Length dependence kinetics of poly dA segments

| Length of Poly dA | Association rate constant ($k_{on}$ (M$^{-1}$s$^{-1}$)) |
| --- | --- |
| 10 | 1.3 × 10$^7$ |
| 15 | 5.3 × 10$^7$ |
| 20 | 9.5 × 10$^7$ |

Conclusion. Poly dA$_{15}$ exists as a structured single helix at neutral pH (24-27). We have shown that at acidic pH, poly dA forms a right-handed parallel-stranded double helix which we term the A-motif. As evidenced by NMR, the poly dA$_{15}$ duplex is held together by reverse Hoogsteen base-pairing between protonated adenosines, with molecular dynamics studies also suggesting electrostatic interactions between the phosphate backbone and N1-H$^+$ of the base. We have delineated the structure of the poly dA$_{15}$ duplex and from MD simulations, also present an atomistic model of such right-handed, parallel-stranded duplexes previously referred to as Π-DNA (29). The thermal stability of the dA$_{15}$ A-motif was found to be ~80° C. as probed by both CD spectroscopy and UV spectrophotometry. The melting temperature, T$_{1/2}$ was found to be dependent on concentration indicating the intermolecular nature of the A-motif. Fluorescence quenching experiments on the parallel dA$_{15}$ duplex indicated that at these segment lengths, slipped hybridizations were insignificant.

Importantly we have demonstrated that dA$_{15}$ undergoes a pH-induced molecular transition from its single helical to duplex form efficiently and reversibly. The kinetics of association to form the A-motif is complete within millisecond time scale at sub-micromolar concentrations. We have also shown that dA$_{15}$ can be used as a proton driven molecular switch that switches reproducibly between its single helical and duplex forms with negligible loss of efficiency. The switching is two-state and is highly processive. As a switch, the A-motif has properties which would make it a valuable addition to the structural DNA nanotechnology toolkit. It has all the advantages of proton driven switches, being 'clean', generating only water and salt as by-products for each cycle of switching. Although slipped hybridizations could occur, these happen only in longer dA tracts, and may be avoided by employing shorter A-tracts that include a CGA motif at the 5' end (29) to keep the strands in register. Apart from its high stability, it is simple to construct, composed of just one type of DNA base, thus minimizing interference upon its incorporation as part of a larger DNA assembly. Because it is a non-Watson-Crick-based building block, it can be integrated into Watson-Crick base-paired assemblies to realize switches with more complex functionalities.

Thus we have outlined the molecular basis of a new pH-sensitive DNA structural motif and shown its successful working as a high-performance pH-triggered molecular switch, undergoing a transition between two well-defined states triggered by a change in pH. This also represents a new mechanism by which two DNA strands may hybridize and dissociate triggered by pH, finding application as a unique method to site-specifically glue DNA assemblies together on providing a pH cue. It can thus be used to replace a critically positioned Watson-Crick base-pairing site on a given DNA assembly transforming it into a sticky or nonsticky state on the application of an external pH stimulus. Thus, with the A-motif, we can build pH responsive 1D, 2D and 3D architectures because (i) the base-pairing here requires only two strands, (ii) directionality is conferred by the parallel-stranded nature of the A-motif (as opposed to antiparallel B-DNA) and (iii) this mechanism is compatible with and does not interfere with Watson-Crick base-pairing in an assembly. The observation of millisecond association timescales for the A-motif illustrates the immense potential of non-B-DNA-based modules in structural DNA nanotechnology.

Example 2

Use of A-Motif to Measure Endosomal pH

Cellular processes such as endocytosis show characteristic acidification profiles that are integral to endosome maturation, vesicle and cargo functions such as sorting of secretory molecules, growth factors, nutrients and toxins. There are several mechanisms of endocytosis and of specific interest to the A-motif is the receptor mediated endocytotic pathway. When a specific ligand binds with its receptor, the ligand is internalized by the cell through the formation of a vesicle termed as the early endosome. The early endosome has a pH 6 to 6.5. Rab 5 is a GTPase which is localised in early endosomes and is therefore used as a molecular marker for an early endosome. The early endosome gradually matures to late endosome and lysosome which is identified by LysoTracker™ red staining.

As early endosomes mature to late endosomes and finally to lysosomes, they undergo a characteristic change of pH ranging from 6-6.2 in early endosomes, to pH 5.5 and 5 in the late endosome and lysosome respectively. The capacity of the A-motif to function inside living cells is investigated by detecting endosome maturation in *Drosophila* hemocytes. *Drosophila* hemocytes are 'pulsed' or incubated with a mixture of poly $dA_{15}$ labeled with Bodipy TMR (80 nM) and FITC-Dextran (1 mg/mL), a marker of the endosomal fluid phase. *Drosophila* hemocytes are pulsed (5 min) and chased for 5 min, fixed and imaged in a confocal microscope. It is predicted that the poly $dA_{15}$ will be found to be localized in distinct punctate structures ~1 µm in size. When these images are overlayed with co-internalized FITC-Dextran images, these puncta will be found to colocalize (~90%), indicating that the poly $dA_{15}$ indeed enters endosomes.

Example 3

Visualizing pH Changes in Cells and Tissues of Whole Organisms

In order to test the ability of the A-motif to detect pH changes in whole organisms, the A-motif is injected into *C. elegans*. Briefly, the A-motif solution of Example 1 is injected into *C. elegans*. It is predicted that the sensor will be found to localize to the coelomocytes of the organism, where it is endocytosed. Once localized to the endosomes, a conformational shift in the A-motif results in significant fluorescence clearly marking the endosomes in the coelomocytes of *C. elegans*. Accordingly, the A-motif can be used to visualize the pH changes of tissues and cellular compartments within a living organism. Moreover, by attaching the appropriate tag or targeting moiety to the A-motif, it may be possible to target the A-motif to various tissues or cell-types, such as neurons. As such, the A-motif is useful in the claimed methods to measure the pH of tissues and cells in whole organisms.

Example 4 pH Toggled Rigid DNA Architectures: Reversible Assembly of 3WJs

In this Example, we demonstrated a strategy to build a reversibly self assembled rigid 1D DNA architecture. This is the first demonstration of reversible assembly and complete disassembly of a defined 1D architecture into its building block. Both steps are controllable by a pH toggle that switches ON and OFF an unusual mode of DNA hybridization, namely A-motif formation. Importantly, complex building blocks may be oligomerized by A-motif formation with as much fidelity as seen in Watson Crick hybridization.

DNA strands were purchased from Bioserve India Ltd and MWG (India). Three way junctions (123, 123A, 123T and 12SH3A) were constructed in 100 µM concentration by annealing an equimolar mixture of oligo 1 (SEQ ID NO: 7), 2 (SEQ ID NO: 6) or 2SH and either of 3 (SEQ ID NO: 8), 3A (SEQ ID NO: 5) or 3T (SEQ ID NO: 9) from 90° C. to 25° C. in pH 7.5 water in presence of 10 mM NaCl and 5 mM $MgCl_2$. 100 mM Sodium Citrate buffer of pH 2.5 was used for pH jump to pH 3.5.

Figure 22:
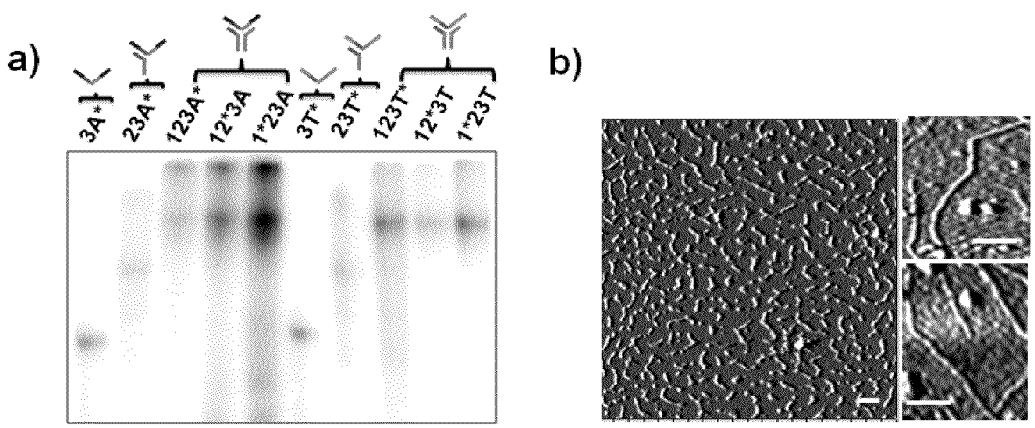
FIG. 22 shows illustrative autoradiogram and AFM images of 5 μM 123A at pH 3.5. a) 10% Native PAGE run in RB buffer pH 3.5. Lane 1: 3A*, 2: 23A*, 3: 123A*, 4: 12*3A, 5: 1*23A, 6: 3T* 7: 23T*, 8: 123T*, 9: 12*3T, 10: 1*23T (* is γ-P32 labeled oligonucleotide). b) Tapping mode AFM images of 5 μM 123A at pH 3.5 deposited on mica. Scale bar: 500 nm.

In order to see whether 123A could associate to form a higher order structure (HOS) we lowered the pH of 5 µM 123A, 10 mM NaCl, 5 mM $MgCl_2$, pH 7.5 to pH 3.5 by addition of 5 µL 100 mM sodium citrate buffer (pH 2.5) into 50 µL solution. We investigated the sample by gel electrophoresis at pH 3.5. Interestingly, 123A at pH 3.5 showed an extra band with significantly reduced mobility (FIG. 22A) as compared to 123A at pH 8.3. These low mobility bands comprise all three component oligonucleotides of the 3WJ suggesting the formation of a HOS by 123A. Importantly, 123T or 123 when, subjected to the same conditions did not show any such low mobility species but existed as isolated 3WJ complexes (FIG. 22A).

In order to understand the broad nature of these HOS, we subjected a solution of 123A at pH 3.5 to Atomic Force Microscopy (AFM). Interestingly, the AFM images of 5 µM 123A at pH 3.5 showed several wire like features of average length ~500 nm (FIG. 22B). Importantly, AFM also revealed longer wires upto 2-3 microns (FIG. 22B, right panel). However, these were much smaller in frequency. With 123T and 123 under identical conditions, we did not observe any wire like feature. Taken together, gel electrophoresis and AFM indicate that the AFO functionalized 3WJ (123A) associates into wire like HOS at pH 3.5.

Figure 23:
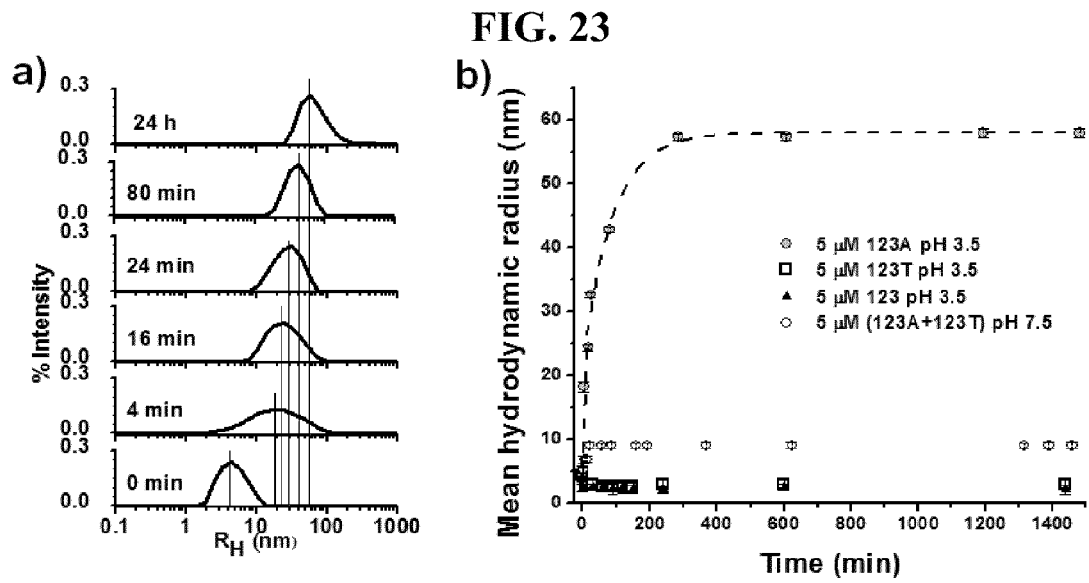
FIG. 23 shows illustrative graphs of the formation of HOS by Dynamic Light Scattering showing a) Shift in distribution of hydrodynamic radius of 50 μM 123A with time upon lowering pH. b) Time dependent growth of HOS by 123A monitored by mean $R_H$ at lower pH. 123 and 123T did not show any increase in $R_H$ value upon lowering pH.

Notably, there is a substantial disproportionation of the HOS into monomers during gel electrophoresis as the A-motif is destabilized at salt concentrations greater than 50 mM. Thus gel electrophoresis becomes unsuitable when eliciting quantitative information in bulk on A-motif mediated association. Therefore, we have quantified oligomerization of 123A using a more ideally suited, complementary, bulk method namely Dynamic Light Scattering (DLS). In this system, oligomerization gives rise to a linear polymer as evidenced by AFM. Since linear polymers collapse into entropic coils of hydrodynamic radius $RH \propto (LPLC)1/2$ where LC is the contour length and Lp is persistence length of the polymer, the growth of this HOS can be monitored by following the increase of RH of a given solution of 123A as a function of time. At pH 7.5, 5 µM of 123A, shows a RH of 4.4 nm which is consistent with its existence as a monomer 3WJ (FIG. 23A, bottom trace). Upon lowering the pH of solution containing 5 µM 123A from 7.5 to 3.5, the mean of the distribution of RH shifted to progressively higher values with increasing time (FIG. 23A, upper traces). A plot of the mean RH values with time, reveals a steady increase in RH from 4.4 nm to 58 nm over ~300 min after the pH jump beyond which it saturates (FIG. 23B). Importantly, 123T and 123, at pH 3.5 showed RH values of 2.8 nm and 2.5 nm which are consistent with size of their monomeric 3WJ states at pH 7.5 (FIG. 23B). The degree of oligomerization in the HOS formed by 5 µM of 123A at pH 3.5 was determined to be ~23 monomeric units on average. This indicates that the association of 123A at pH 3.5 into HOS is a bulk phenomenon. Just as a comparison of A-motif duplexation-based self assembly and Watson-Crick base-paired self-assembly, we also monitored the growth of a mixture of 123A and 123T at pH 7.5, where the total building block concentration is 5 µM (FIG. 23B). This also showed an initial RH increase which plateaus at RH of 9.1 nm, leading to no further increase even after 48 hrs. This shows that A-motif mediated assembly leads to more extended HOS than Watson-Crick based hybridization of building blocks under these conditions. The HOS formed in a mixture of 123A and 123T after 48 hrs incubation at 25° C. showed retarded gel mobility as compared to 123A and 123T alone.

In summary, these data show that the sequence of AFOs is simple, non-interfering and thus can be easily integrated into precharacterized B-DNA based tiles. Thus this method can be used to make pH toggled 2D and 3D rigid scaffolds that may be reversibly assembled by controlling pH. Given the advantages of the non-toxic working cycle of the A-motif and its integratability to B-DNA based hybridization assemblies, DNA walkers incorporating A-motif based feet could increase processivity as well as directionality of walkers that currently use only B-DNA based feet. A-motif formation could aid movement using a chemical fuel without affecting the track thus increasing processivity. Thus, a combination of B-DNA and A-motif forming sequences can be used to achieve greater control of nanoscale movement of DNA devices in terms of directionality and processivity. This will be a valuable addition to the current toolbox to make functional DNA nano-architectures.

REFERENCES

1. Bath J, Turberfield A J. DNA nanomachine. *Nat. Nanotech.* (2007) 2:275-284.
2. Pitchiaya S, Krishnan Y. First blueprint, now bricks: DNA as construction material on the nanoscale. *Chem. Soc. Rev.* (2006) 35:1111-1121.
3. Samori B, Zuccheri G. DNA codes for nanoscience. *Angew. Chem. Int. Ed. Eng.* (2005) 44:1166-1181.
4. Seeman N C. Biochemistry and structural DNA nanotechnology: an evolving symbiotic relationship. *Biochemistry* (2003) 42:7259-7269.
5. Liu H, Xu Y, Li F, Yang Y, Wang W, Song Y, Liu D. Light-driven conformational switch of i-motif DNA. *Angew. Chem. Int. Ed.* (2007) 46:2515-2517.
6. Liedl T, Simmel F C. Switching the conformation of a DNA molecule with a chemical oscillator. *Nano Lett.* (2005) 5:1894-1898.
7. Chan Y, Lee S H, Mao C. A DNA nanomachine based on a duplex-triplex transition. *Angew. Chem. Int. Ed.* (2004) 43:5335-5338.
8. Liu D, Balasubramanian S. A proton-fueled DNA nanomachine. *Angew. Chem. Int. Ed.* (2003) 42:5734-5736.
9. Alberti P, Mergny J L. DNA duplex-quadruplex exchange as the basis for a nanomolecular machine. *Proc. Natl Acad. Sci. USA* (2003) 100:1569-1573.
10. Mao C, Sun W, Shen Z, Seeman N C. A nanomechanical device based on the B-Z transition of DNA. *Nature* (1999) 397:144-146.
11. Monchaud D, Yang P, Lacroix L, Teulade-Fichou M P, Mergny J L. A metal-mediated conformational switch controls G-quadruplex binding affinity. *Angew. Chem. Int. Ed.* (2008) 47:4858-4861.
12. Gehring K, Leroy J L, Guéron M. A tetrameric DNA structure with protonated cytosine.cytosine base pairs. *Nature* (1993) 363:561-565.
13. Snoussi K, Nonon-Lacomte S, Leroy J L. The RNA i-motif. *J. Mol. Biol.* (2001) 309:139-153.
14. Sen D, Gilbert W. Formation of parallel four-stranded complexes by guanine-rich motifs in DNA and its implications for meiosis. *Nature* (1988) 334:364-364.
15. Zimmerman S B, Cohen G H, Davies D R. X-ray fibre diffraction and model-building study of polyguanylic acid and polyinosinic acid. *J. Mol. Biol.* (1975) 92:181-192.
16. Gellert M, Lipsett M N, Davies D R. Helix formation by guanylic acid. *Proc. Natl Acad. Sci. USA* (1962) 48:2013-2018.
17. Rich A, Davies D R, Crick F H C, Watson J D. The molecular structure of polyadenylic acid. *J. Mol. Biol.* (1961) 3:71-86.
18. Fresco J R. Polynucleotides. II. The x-ray diffraction patterns of solutions of the randomly coiled and helical forms of polyriboadenylic acid. *J. Mol. Biol.* (1959) 1:106-110.
19. Ts'o P O P, Helmkamp G K, Sander C. Interaction of nucleosides and related compounds with nucleic acids as indicated by the change of helix-coil transition temperature. *Proc. Natl Acad. Sci. USA* (1962) 48:686-697.
20. Zimmerman S B, Davies D R, Navia M A. An ordered single-stranded structure for polyadenylic acid in denaturing solvents. An X-ray fibre diffraction and model building study. *J. Mol. Biol.* (1977) 116:317-330.
21. Saenger W, Riecke J, Suck D. A structural model for the polyadenylic acid single helix. *J. Mol. Biol.* (1975) 93:529-534.
22. Sachs A, Wahle E. Poly(A) tail metabolism and function in eucaryotes. *J. Biol. Chem.* (1993) 268:22955-22958.
23. Le H, Browning K S, Gallie D R. The phosphorylation state of poly(A)-binding protein specifies its binding to poly(A) RNA and its interaction with eukaryotic initiation factor (eIF) 4F, eIFiso4F, and eIF4B. *J. Biol. Chem.* (2000) 275:17452-17462.
24. Bush C A, Scheraga H A. Optical activity of single-stranded polydeoxyadenylic and polyriboadenylic acids; dependence of adenine chromophore cotton effects on polymer conformation. *Biopolymers* (1969) 7:395-409.
25. Alderfer J L, Smith S L. A proton magnetic resonance study of polydeoxyriboadenylic acid. *J. Am. Chem. Soc.* (1971) 93:7305-7314.
26. Olsthoorn C S M, Bostelaar L J, vanBoom H, Altona C. Conformational characteristics of the trinucleoside diphosphate dApdApdA and its constituents from nuclear magnetic resonance and circular dichroism studies. Extrapolation to the stacked conformers. *Eur. J. Biochem.* (1980) 112:95-110.
27. Ke C, Humeniuk M, S-Gracz H, Marszalek P E. Direct measurements of base stacking interactions in DNA by single-molecule atomic-force spectroscopy. *Phys. Rev. Lett.* (2007) 99:018302-018305.
28. Luo J, Sarma M H, Yuan R D, Sarma R H. R study of self-paired parallel duplex of d(AAAAACCCCC) in solution. *FEBS Lett.* (1992) 306:223-228.
29. Robinson H, Wang A H-J. 5'-CGA sequence is a strong motif for homo base-paired parallel-stranded DNA duplex as revealed by NMR analysis. *Proc. Natl Acad. Sci. USA* (1993) 90:5224-5228.

30. Wang Y, Patel D J. Solution structure of the d(T-C-G-A) duplex at acidic pH. A parallel-stranded helix containing $C^+.C$, G.G and A.A pairs. *J. Mol. Biol.* (1994) 242:508-526.
31. Chakraborty S, Modi S, Krishnan Y. The $RNA_2$-$PNA_2$ hybrid i-motif-a novel RNA-based building block. *Chem. Commun.* (2008) 70-72.
32. Ghodke H B, Krishnan R, Vignesh K, Kumar G V P, Narayana C, Krishnan Y. The I-tetraplex building block: rational design and controlled fabrication of robust 1D DNA scaffolds through non-Watson-Crick interactions. *Angew. Chem. Int. Ed.* (2007) 46:2646-2649.
33. Modi S, Wani A H, Krishnan Y. The PNA-DNA hybrid I-motif: implications for sugar-sugar contacts in i-motif tetramerization. *Nucleic Acids Res.* (2006) 34:4354-4363.
34. Krishnan-Ghosh Y, Stephens E, Balasubramanian S. PNA forms an i-motif. *Chem. Commun.* (2005) 5278-5280.
35. Krishnan-Ghosh Y, Liu D, Balasubramanian S. Formation of an interlocked quadruplex dimer by d(GGGT). *J. Am. Chem. Soc.* (2004) 126:11009-11016.
36. Mills J B, Vacano E, Hagerman P J. Flexibility of single-stranded DNA: use of gapped duplex helices to determine the persistence lengths of poly(dT) and poly(dA). *J. Mol. Biol.* (1999) 285:245-257.
37. Case D A, Pearlman D A, Caldwell J W, Cheatham T E, Wang J, Ross W S, Simmerling C, Darden T, Merz K M, Stanton R V, et al. AMBER 7 edit. (1999) San Francisco: University of California.
38. Duke R E, Pedersen L G. *PMEMD* 3. (2003) University of North Carolina-Chapel Hill.
39. Maiti P K, Pascal T A, Vaidehi N, Goddard W A. The stability of Seeman JX DNA topoisomers of paranemic crossover (PX) molecules as a function of crossover number. *Nucleic Acids Research* (2004) 32:6047-6056.
40. Maiti P K, Bagchi B. Structure and dynamics of DNA-dendrimer complexation: role of counterions, water, and base pair sequence. *Nano. Lett.* (2006) 6:2478-2485.
41. Delano W L. The PyMOL molecular graphics system. (2002) San Carlos, Calif., USA: DeLano Scientific.
42. Pettersen E F, Goddard T D, Huang C C, Couch G S, Greenblatt D M, Meng E C, Ferrin T E. UCSF Chimera-a visualization system for exploratory research and analysis. *J. Comput. Chem.* (2004) 25:1605-1612.
43. Hwang T L, Shaka A J. Water suppression that works. Excitation sculpting using arbitrary wave-forms and pulsed-field gradients. *J. Magnetic Res. Ser. A* (1995) 112: 139-282.
44. Adler A J, Grossman L, Fasman G D. Polyriboadenylic and polydeoxyriboadenylic acids. Optical rotatory studies of pH-dependent conformations and their relative stability. *Biochemistry* (1969) 8:3846-3859.
45. Brahms J, Michelson A M, van Holde K E. Adenylate oligomers in single- and double-strand conformation. *J. Mol. Biol.* (1966) 15:467-488.
46. Janik B, Sommer R G, Bobst A M. Polarography of polynucleotides. II. Conformations of poly(adenylic acid) at acidic pH. *Biochim. Biophys. Acta.* (1972) 281:152-168.
47. Bernacchi S, Mély Y. Exciton interaction in molecular beacons: a sensitive sensor for short range modifications of the nucleic acid structure. *Nucleic Acids Res.* (2001) 29:e62.
48. Chakraborty S, Krishnan Y. Kinetic hybrid i-motifs: intercepting DNA with RNA to form a $DNA_2$-$RNA_2$ i-motif. *Biochimie* (2008) 90:1088-1095.
49. C. A. Bush & H. A. Scheraga, *Biopolymers,* 1969, 7, 395-409.
50. J. L. Alderfer & S. L. Smith, *J. Am. Chem. Soc.* 1971, 93, 7305-7314.
51. A. Rich, D. R. Davies, F. H. C. Crick, J. D. Watson, *J. Mol. Biol.* 1961, 3, 71-86.
52. a) S. Bernacchi, Y. Mély, *Nucleic Acids Res.* 2001, 29, e62; b) S. Modi, A. H. Wani, Y. Krishnan, *Nucleic Acids Res.* 2006, 34, 4354-4363; c) S. Chakraborty, S. Modi, Y. Krishnan, *Chem. Commun.* 2008, 70-72; d) S. Chakraborty & Y. Krishnan, *Biochimie,* 2008, 90, 1088-1095.
53. G. G. Dvoryantseva, T. N. Ul'yanova, T. Ya. Filipenko, M. P. Nemeryuk, T. S. Safonova, Y. N. Sheinker, P. V. Petrovskii, E. I. Fedin, *Khim. Geterotsikl. Soedin.* 1977, 1, 49-54.
54. M. W. Germann, N. Zhou, J. H. van de Sande, and H. J. Vogel, Methods in Enzymology, 1995, 261, 207-225.
55. D. A. Case et al., AMBER 8.0, 1999, University of California, San Francisco, Calif.
56. C. S. Tung and E. S. Carter, *CABIOS,* 1994, 10, 427.
57. M. J. Frisch, et al., Gaussian 03, Revision C.01, Gaussian, Inc., Wallingford Conn., 2004.
58. J. Wang, W. Wang, P. A. Kollman, D. A. Case, *Journal of Molecular Graphics and Modeling,* 2006, 25, 247.
59. P. Cieplak, W. D. Cornell, C. Bayly & P. A. Kollman, *J. Comp. Chem.* 1995, 16, 1357-1377.
60. W. L. Jorgensen, J. Chandrasekhar, J. D. Madura, R. W. Impey and M. L. Klein, *J. Chem. Phys.* 1983, 79, 926-935.
61. P. K. Maiti, T. A. Pascal, N. Vaidehi, et al. *Nucleic Acids Res.* 2004, 32, 6047.
62. P. K. Maiti and B. Bagchi, *Nano. Letts,* 2006, 6, 2478.
63. Y. Duan, C. Wu, S. Chowdhury, M. C. Lee, G. Xiong, W. Zhang, R. Yang, P. Cieplak, R. Luo, T. Lee, *J. Comput. Chem.* 2003, 24, 1999.
64. U. Essmann, L. Perera, M. L. Berkowitz, et al., *J. Chem. Phys.* 1995, 103, 8577.
65. W. K. Olson, *Nucleic Acids Res.* 1975, 2, 2055-2068; B. S. Stannard and G. Felsenfeld, *Biopolymers,* 1975, 14, 299-307.
66. R. Lavery and H. Sklenar *J. Biomol. Struct. Dynam.* 1989, 6, 655-667.
67. E. Carrillo-Nava, Y. Mejia-Radillo and H-J. Hinz, *Biochemistry,* 2008, 47, 13153-13157.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 particles refers to groups having 1, 2, or 3 particles. Similarly, a group having 1-5 particles refers to groups having 1, 2, 3, 4, or 5 particles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference in their entireties and for all purposes to the same extent as if each individual publication, patent, or patent application was specifically and individually incorporated by reference in its entirety for all purposes.

What is claimed is:

1. A molecular switch comprising at least two poly dA nucleic acids, wherein the at least two poly dA nucleic acids transition between first and second stable conformations in response to a change in pH, and wherein said molecular switch comprises a signaling system.

2. The molecular switch of claim 1, wherein the at least two poly dA nucleic acids each comprise at least 10 consecutive dA nucleobases.

3. The molecular switch of claim 1, wherein said first and second conformations comprise a parallel-stranded double helix and a single helix, respectively.

4. The molecular switch of claim 1, wherein the at least two poly dA nucleic acids are in a parallel-stranded double helix conformation at acidic pH.

5. The molecular switch of claim 1, wherein the at least two poly dA nucleic acids are in single helix conformation at neutral pH.

6. The molecular switch of claim 1, wherein the signaling system comprises an interacting label pair.

7. The molecular switch of claim 6, wherein the interacting label pair is capable of energy transfer.

8. The molecular switch of claim 7, wherein the interacting label pair is a fluorophore and quencher pair.

9. The molecular switch of claim 8, wherein the fluorophore and the quencher are on separate poly dA nucleic acids, such that a difference in a fluorescent signal is detectable upon a change in conformation of the molecular switch.

10. The molecular switch of claim 8 further comprising a tagging moiety for linking the molecular switch to other biomolecules.

11. A nucleic acid assembly comprising one or more modules comprising an A-motif forming nucleic acid, wherein the A-motif forming nucleic acid transitions between first and second stable conformations in response to a change in pH in order to join the modules in a nucleic acid assembly.

12. The nucleic acid assembly of claim 11, wherein two or more modules are joined to form a 1D, 2D or 3D architecture.

13. The nucleic acid assembly of claim 11, wherein the module comprises a molecular structure selected from the group consisting of a single stranded nucleic acid, a double-stranded nucleic acid, and a polypeptide.

14. The nucleic acid assembly of claim 11, wherein the module comprises a nucleic acid polymer capable of undergoing Watson-Crick base pairing.

15. The nucleic acid assembly of claim 11, wherein at least one module is linked to a substrate.

16. A method for determining the pH of a sample, the method comprising:
    contacting the sample with one or more indicators having at least two poly dA nucleic acid strands conjugated to a signaling system, wherein the one or more indicators transition between first and second stable conformations in response to a changin pH; and
    detecting the presence, absence, or magnitude of a signal from the signaling system to determine the pH of the sample.

17. The method of claim 16, wherein the detecting comprises measuring the magnitude of the signal generated, wherein the magnitude indicates the pH of the sample.

18. The method of claim 16, wherein the magnitude of the signal changes as the pH varies from pH 2 to 10.

19. The method of claim 16, wherein the magnitude of the signal changes as the pH varies from pH 5 to 7.

* * * * *

UNITED STATES PATENT AND TRADEMARK OFFICE
CERTIFICATE OF CORRECTION

PATENT NO. : 8,153,437 B2
APPLICATION NO. : 12/720952
DATED : April 10, 2012
INVENTOR(S) : Krishnan et al.

It is certified that error appears in the above-identified patent and that said Letters Patent is hereby corrected as shown below:

On Page 2, in Field (56), under "OTHER PUBLICATIONS", in Column 1, Line 27, delete "Nanphagocytic" and insert -- Nonphagocytic --, therefor.

On Page 2, in Field (56), under "OTHER PUBLICATIONS", in Column 2, Line 42, delete "Eucaryotes,"" and insert -- Eukaryotes," --, therefor.

Figure 8:
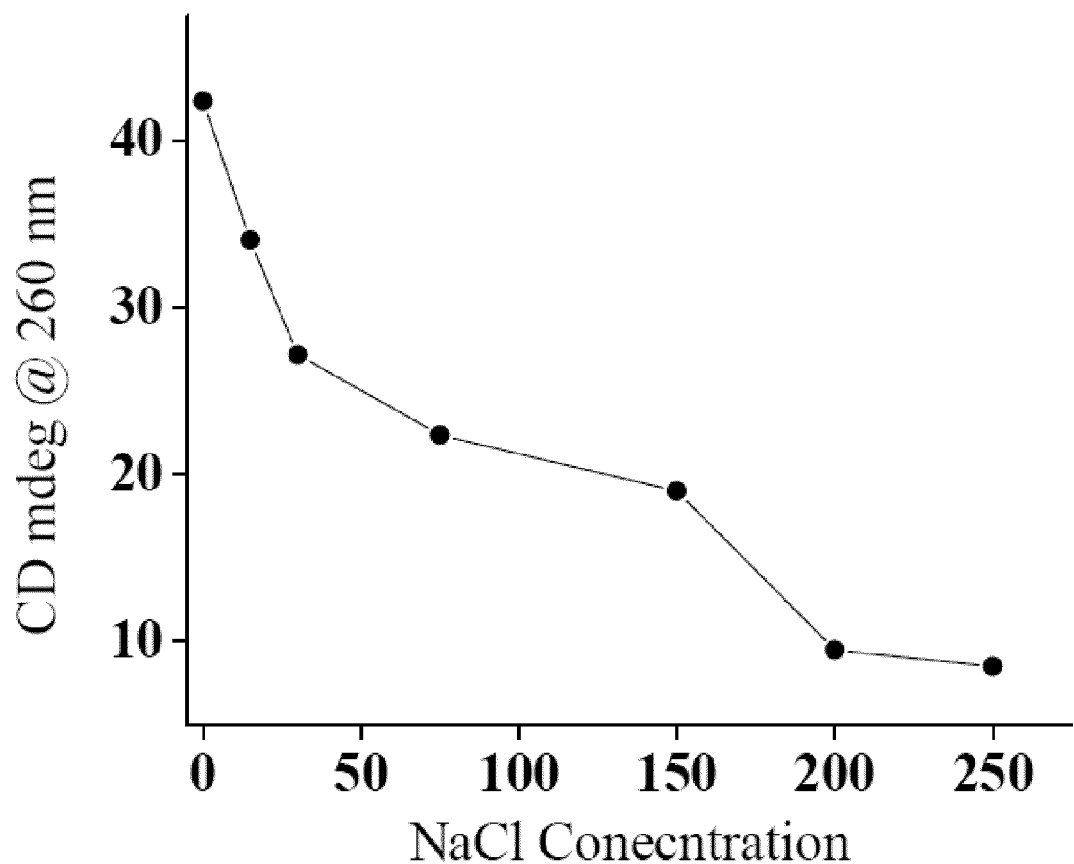
FIG. 8 is a graph illustrating the effect of salt on CD spectra of $dA_{15}$ duplex in unbuffered pH 3 water.

In Fig. 8, Sheet 9 of 20, delete "Conecntration" and insert -- Concentration --, therefor.

In Column 3, Line 50, delete "follows." and insert -- follows: --, therefor.

In Column 5, Line 38, delete "c)" and insert -- (c) --, therefor.

In Column 19, Line 19, delete "dA 15" and insert -- $dA_{15}$ --, therefor.

In Column 19, Line 59, delete "NaOH)" and insert -- NaOH] --, therefor.

In Column 24, Line 8, delete "of5'-TAMRA-" and insert -- of 5'-TAMRA- --, therefor.

In Column 27, Line 42, delete "at" and insert -- al. --, therefor.

In Column 34, Line 38, delete "eucaryotes."" and insert -- eukaryotes." --, therefor.

In Column 41, Line 11, in Claim 10, delete "8" and insert -- 1 --, therefor.

In Column 42, Line 12, in Claim 16, delete "changein" and insert -- change in --, therefor.

Signed and Sealed this
Eighth Day of January, 2013

David J. Kappos
*Director of the United States Patent and Trademark Office*

```
                        SEQUENCE LISTING

<160> NUMBER OF SEQ ID NOS: 9

<210> SEQ ID NO 1
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 1
aaaaaaaaaa aaaaa                                                        15

<210> SEQ ID NO 2
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (15)..(15)
<223> OTHER INFORMATION: Dabcyl-labeled A nucleotide

<400> SEQUENCE: 2
aaaaaaaaaa aaaaa                                                        15

<210> SEQ ID NO 3
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (15)..(15)
<223> OTHER INFORMATION: TMR-labeled A nucleotide

<400> SEQUENCE: 3
aaaaaaaaaa aaaaa                                                        15

<210> SEQ ID NO 4
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: TAMRA-labeled A nucleotide
```

```
<400> SEQUENCE: 4
aaaaaaaaaa aaaaa                                                     15

<210> SEQ ID NO 5
<211> LENGTH: 74
<212> TYPE: DNA
<213> ORGANISM: Artificial Sequence
<220> FEATURE:
<223> OTHER INFORMATION: Synthetic oligonucleotide

<400> SEQUENCE: 5
aaaaaaaaaa aaaaaacatg ccggtattta aagcctttcg aagatatcgt ggttcgagaa    60
aaaaaaaaaa aaaa                                                      74

<210> SEQ ID NO 6
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 6
cgagctgcag cagctgttat ttaggcttta ataccggca tg                        42

<210> SEQ ID NO 7
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 7
ctcgaaccac gatatcttcg ttataacagc tgctgcagct cg                       42

<210> SEQ ID NO 8
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 8
atgccggtat ttaaagcctt tcgaagatat cgtggttcga g                        41

<210> SEQ ID NO 9
<211> LENGTH: 74
<212> TYPE: DNA
<213> ORGANISM: Artificial Sequence
<220> FEATURE:
<223> OTHER INFORMATION: Synthetic oligonucleotide

<400> SEQUENCE: 9
tttttttttt tttttcatg ccggtattta aagcctttcg aagatatcgt ggttcgagtt    60
tttttttttt tttt                                                      74
```